(12) United States Patent
Smith et al.

(10) Patent No.: US 6,310,199 B1
(45) Date of Patent: Oct. 30, 2001

(54) PH DEPENDENT ION EXCHANGE MATRIX AND METHOD OF USE IN THE ISOLATION OF NUCLEIC ACIDS

(75) Inventors: Craig E. Smith, Oregon, WI (US); Diana L. Holmes, Crystal Lake, IL (US); Daniel J. Simpson, Middleton, WI (US); Jehoshua Katzenhendler, Jerusalem, IL (US); Rex M. Bitner, Cedarburg; Josephine C. Grosch, Mazomainie, both of WI (US)

(73) Assignee: Promega Corporation, Madison, WI (US)

(*) Notice: Subject to any disclaimer, the term of this patent is extended or adjusted under 35 U.S.C. 154(b) by 0 days.

(21) Appl. No.: 09/312,172

(22) Filed: May 14, 1999

(51) Int. Cl.[7] ............... C07G 3/00; C12Q 1/68; C07H 21/00; C07H 21/02; C07H 21/04

(52) U.S. Cl. ............ 536/25.4; 435/6; 536/18.5; 536/25.41

(58) Field of Search ............... 435/6; 536/25.4, 536/18.5, 25.41

(56) References Cited

U.S. PATENT DOCUMENTS

| 4,233,169 | 11/1980 | Beall et al. | 252/62.59 |
| 4,297,337 | 10/1981 | Mansfield et al. | 424/1 |
| 4,395,271 | 7/1983 | Beall et al. | 65/31 |

(List continued on next page.)

FOREIGN PATENT DOCUMENTS

| 2223821 | 6/1996 | (CA) . |
| DE 43 07 262 A1 | 9/1994 | (DE) . |
| 0757106A2 | 2/1997 | (EP) . |

(List continued on next page.)

OTHER PUBLICATIONS

Bischoff, Rainer and Larry W. McLaughlin. Nucleic Acid Resolution By Mixed–Mode Chromatography. *Journal of Chromatography* (1984) 296:329–337.

Bischoff, Rainer and Larry W. McLaughlin. Chemically Synthesized Hydrophobic Anion–Exhange High–Performance Liquid Chromatography Supports Used for Oligonucleotide Resolution By Mixed Mode Chromatography. *Journal of Chromatogrpaphy*. (1983) 270:117–126.

Cotton, M. et al., 1994, *Gene Therapy* 1:239–246.

(List continued on next page.)

*Primary Examiner*—Ardin H. Marschel
(74) *Attorney, Agent, or Firm*—Michael Best & Friedrich LLP; Grady J. Frenchick; Karen B. King

(57) ABSTRACT pH dependent ion exchange matrices are provided, with methods for making such matrices, and methods for using such matrices to isolate a target nucleic acid, such as plasmid DNA, chromosomal DNA, or RNA from contaminants, including proteins, lipids, cellular debris, or other nucleic acids. Each pH dependent ion exchange matrix of this invention comprises at least two different ion exchange functional groups, one of which is capable of acting as an anion exchanger at a first pH, and the other of which is capable of acting as a cation exchanger at a second, higher pH. The matrix has an overall neutral charge in a pH range between the first and second pH. The pH dependent ion exchange matrices of the present invention are designed to bind to the target nucleic acid at a pH wherein the overall charge of the matrix is positive, and to release the target nucleic acid as the pH of the surrounding solution is increased. The target nucleic acid can be released from the pH dependent matrix in little or no salt and at about a neutral pH. The matrices and methods of this invention enable one to isolate a target nucleic acid in very few steps, without the use of hazardous chemicals. Target nucleic acids isolated using the pH dependent ion exchange matrices according to the present invention can be used immediately without further extraction or isolation.

70 Claims, 4 Drawing Sheets

U.S. PATENT DOCUMENTS

| | | | |
|---|---|---|---|
| 4,523,996 | 6/1985 | Charles et al. | 210/504 |
| 4,672,040 | 6/1987 | Josephson | 436/526 |
| 4,683,202 | 7/1987 | Mullis | 435/91 |
| 4,695,393 | 9/1987 | Whitehead et al. | 252/62.54 |
| 4,699,717 | 10/1987 | Riesner et al. | 210/635 |
| 4,767,670 | 8/1988 | Cox et al. | 428/403 |
| 5,057,426 | 10/1991 | Henco et al. | 435/270 |
| 5,075,430 | 12/1991 | Little | 536/27 |
| 5,076,950 | 12/1991 | Ullman et al. | 252/62.51 |
| 5,155,018 | 10/1992 | Gillespie et al. | 435/91 |
| 5,234,809 | 8/1993 | Boom et al. | 435/91 |
| 5,316,680 | 5/1994 | Frechet et al. | 210/635 |
| 5,346,994 | 9/1994 | Chomczynski | 530/419 |
| 5,389,449 | 2/1995 | Afeyan et al. | 428/523 |
| 5,395,498 | 3/1995 | Gombinsky et al. | 204/182.8 |
| 5,523,231 | 6/1996 | Reeve | 435/270 |
| 5,582,988 | 12/1996 | Backus et al. | 435/6 |
| 5,585,236 | 12/1996 | Bonn et al. | 435/5 |
| 5,610,274 | 3/1997 | Wong | 530/334 |
| 5,652,348 | 7/1997 | Burton et al. | 536/20 |
| 5,658,548 | 8/1997 | Padhye et al. | 423/335 |
| 5,660,984 | 8/1997 | Davis et al. | 435/6 |
| 5,681,946 | 10/1997 | Reeve | 536/25.4 |
| 5,728,822 | 3/1998 | Macfarlane | 536/25.41 |
| 5,734,020 | 3/1998 | Wong | 530/350 |
| 5,747,663 | 5/1998 | Colpan et al. | 536/25.4 |
| 5,783,686 | 7/1998 | Gonzalez | 536/25.4 |
| 5,808,041 | 9/1998 | Padye et al. | 536/25.4 |
| 5,898,071 | 4/1999 | Hawkins | 536/25.4 |
| 5,945,525 | 8/1999 | Uematsu et al. | 536/25.42 |
| 5,990,301 | 11/1999 | Colpan et al. | 536/25.4 |
| 6,027,945 | 2/2000 | Smith et al. | 436/526 |

FOREIGN PATENT DOCUMENTS

| | | |
|---|---|---|
| 2 074 892 A | 11/1981 | (GB) . |
| 9327290 | 12/1997 | (JP) . |
| 9327291 | 12/1997 | (JP) . |
| WO 83/03363 | 10/1983 | (WO) . |
| WO 95/06652 | 3/1995 | (WO) . |
| WO 95/21179 | 8/1995 | (WO) . |
| WO 96/16186 | 5/1996 | (WO) . |
| WO 96/36706 | 11/1996 | (WO) . |
| WO 97/29825 | 8/1997 | (WO) . |
| WO 98/31461 | 7/1998 | (WO) . |
| WO 98/31840 | 7/1998 | (WO) . |

OTHER PUBLICATIONS

Crowother, Jonathan B. High–Performance Liquid Chromatographic Separation of Oligonucleotides and Other Nucleic Acid Constituents on Multifunctional Stationary Phases. *Journal of Chromatography* (1983) 282:619–628.

Edwardson P.A.D., et al. Seperation and purification of oligonucleotides using a new bonded–phase packing material. *Journal of Chromatography* (1991)545:79–89.

Floyd, Thomas R. et al., Mixed–Mode Hydrophobic Ion Exchange for the Seperation of Oligonucelotides and DNA Fragments Using HPLC. *Analytical Biochemistry* (1986) 154:570–577.

F. Ausubel et al., eds.,Current Protocols in Molecular Biology, Wiley–Interscience, New York (1993).

Gjerde, Douglas T. Ion Chromatography. Dr. Alfred Hothig Verlag Heidelberg (1987) $2^{nd}$ Edition, New York.

Goldsborough, Mindy D. High Purity Plasmid DNA from Anion Exchange Chromatography. *Focus* (1998) vol. 20 No. 3.

Hirabayashi, Jun, Applied slalom chromatography Improved DNA seperation by the use of columns developed for reversed–phase chromatography. *Journal of Chromatography* (1996) 722:135–142.

Kirk–Othmer Encyclopedia of Chemical Technology, vol. 21, Mary Howe–Grant, ed., John Wiley & Sons, pub. 1997, pp. 1020–1023.

Little, Edward L. Mark S. Jeansonne, and Joe P. Folely. Sequential Multimodal Elution for Pseudomultidimensional Liquid Chromatography on a Single Column. *Anal. Chem* (1991) 63:33–44.

Maa, Yih–fen et al. Rapid high–performance liquid chromatography of nucleic acids with polystyrene–based micropellicular anion exchangers. *Journal of Chromatography* (1990)508:61–73.

Machrey–Nagel homepage on the Internet on Jun. 12, 1998, at http://www.machrey–nagel.com.

McLaughlin L.M., Chem Rev (1989) 89: 309–319, at p. 309.

Molecular Cloning, ed. By Sambrook et al. (1989), pub. By Cold Spring Harbor Press, pp. 1.42–1.50.

Morrison, David C. 1987, *Ann. Rev. Med.* 38:417–32.

Rassi Ziad El, and Csaba Horvath. Tandem Columns and Mixed–Bed Columns in High–Performance Liquid Chromatography of Proteins. *Journal of Chromotography.* (1986) 359:255–264.

W. Jost, et al. *J. Chromatog.* 185 (1979) 403–412.

Northrup et al. (1991) Analytical Chem 63:1350–1354.

Ausubel et al., Current Protocols in Molecular Biology, Ch. 2 (DNA), Ch. 4 (RNA)(1987).

Bitner, et al., "Use of MagnaSil Paramagnetic Particles for Plasmid Purification, PCT Cleanup, and Purification of Dideoxy and Big Dye DNA Sequencing Reaction", *Proceedings of SPIE–Int. Soc. Opt. Eng.* (2000) vol. 3926, No. 3926 pp. 126–33.

Boom, et al., "Rapid and Simple Method for Purification of Nucleic Acids", *J. Clin. Microbiol.* (1990) 28:495–503.

Brown, et al. "Anion–Cation Separations on a Mixed Bed Alumina–Silica Column", *J. Chromatog.* (1989) vol. 466, No. 1+index pp. 291–300.

Kirk–Othmer, Encyclopedia of Chemical Technology, (1997)vol. 21, 4th ed., 1997, pp. 1021–1022.

Marko et al., "A Procedure for the Large–Scale Isolation of Highly Purified Plasmid DNA Using Alkaline Extraction and Binding to Glass Powder", *Anal. Biochem.* (1982)121:382–387.

Promega, Technical Bulletin No. 202 Wizard® Plus Series 9600™ DNA Purification System, (Promega Corp.) (9/98).

Promega, Technical Bulletin No. 225 Wizard® Plus SV Minipreps DNA Purification System, (Promega Corp.) (9/99).

Promega, Technical Bulletin No. 259 Wizard® PureFection Plasmid DNA Purification System, (Promega Corp.) (9/99).

QuantiBlot Human DNA Quantitation System, PE Applied Biosystems, Feb. 5, 1996, pp. 1–5 (http://www.pebio.com/fo/773503/773503.html).

Sambrook, et al., Molecular Cloning a Laboratory Manual, 2nd ed. pp. 1.25–1.28. (1989).

Vogelstein et al., "Preparative and Analytical Purification of DNA from Agarose", *Proc. Natl. Acad. Sci.* (1979) vol. 76, No. 2:615–619.

wherein, $R^1$ is -OH, -OCH$_3$, or -OCH$_2$CH$_3$; and $R^2$ is:

or

SEQUENCE LISTING

<160> NUMBER OF SEQ ID NOS: 2

<210> SEQ ID NO 1
<211> LENGTH: 64
<212> TYPE: DNA
<213> ORGANISM: Homo sapiens
<220> FEATURE:
<223> OTHER INFORMATION: Oligonucleotide primer of the Adenomatous
      Polypoptosis Coli gene

<400> SEQUENCE: 1
ggatcctaat acgactcact ataggaacag accaccatgc aaatcctaag agagaacaac        60
tgtc                                                                    64

<210> SEQ ID NO 2
<211> LENGTH: 24
<212> TYPE: DNA
<213> ORGANISM: Homo sapiens
<220> FEATURE:
<223> OTHER INFORMATION: Oligonucleotide primer of the Adenomatous
      Polypoptosis Coli gene

<400> SEQUENCE: 2
cacaataagt ctgtattgtt tctt                                              24

PH DEPENDENT ION EXCHANGE MATRIX AND METHOD OF USE IN THE ISOLATION OF NUCLEIC ACIDS

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

This invention relates generally to materials and methods for isolating a target nucleic acid, such as plasmid DNA, chromosomal DNA, total RNA, mRNA, or RNA/DNA hybrids from contaminants, such as proteins, lipids, cellular debris, and non-target nucleic acids. This invention relates, particularly, to pH dependent ion exchange matrices with the capacity to adsorb a target nucleic acid in the presence of a solution at a first pH and to desorb the target nucleic acid in the presence of a second solution at a second pH which is different from the first pH. This invention also relates to methods of making and using such pH dependent ion exchange matrices in isolating target nucleic acids.

BACKGROUND OF THE INVENTION

Many molecular biological techniques such as reverse transcription, cloning, restriction analysis, amplification and sequencing require that nucleic acids used in the techniques be substantially free of contaminants capable of interfering with such processing or analysis procedures. Such contaminants generally include substances that block or inhibit chemical reactions, (e.g. substances that block or inhibit nucleic acid hybridizations, enzymatically catalyzed reactions and other types of reactions used in molecular biological techniques), substances that catalyze the degradation or depolymerization of a nucleic acid or other biological material of interest, or substances which block or mask detection of the nucleic acid of interest. Substances of this last type can block or mask by providing a "background" indicative of the presence in a sample of a quantity of a nucleic acid of interest, (also referred to herein as a "target nucleic acid") when the nucleic acid of interest is not, in fact, present in the sample. Contaminants also include macromolecular substances from the in vivo or in vitro medium from which a target nucleic acid is isolated, macromolecular substances such as enzymes, other types of proteins, polysaccharides, or polynucleotides, as well as lower molecular weight substances, such as lipids, low molecular weight enzyme inhibitors, oligonucleotides, or non-target nucleic acids. Contaminants can also be introduced into a target biological material from chemicals or other materials used to isolate the material from other substances. Common contaminants of this last type include trace metals, dyes, and organic solvents.

Obtaining target nucleic acid sufficiently free of contaminants for molecular biological applications is complicated by the complex systems in which the target nucleic acid is typically found. These systems, e.g., cells from tissues, cells from body fluids such as blood, lymph, milk, urine, feces, semen, or the like, cells in culture, agarose or polyacrylamide gels, or solutions in which target nucleic acid amplification has been carried out, typically include significant quantities of contaminants from which the target nucleic acid of interest must be isolated before being used in a molecular biological procedure.

The earliest techniques developed for use in isolating target nucleic acids from such complex systems typically involve multiple organic extraction and precipitation steps. Hazardous chemicals, such as chloroform and phenol or mixtures thereof, were used in most such procedures. Closed circular nucleic acid molecules, such as plasmid DNA, was typically isolated further by ultra-centrifugation of plasmid DNA in the presence of cesium chloride and ethidium bromide. See, e.g., *Molecular Cloning*, ed. by Sambrook et al. (1989), pp. 1.42–1.50. Ethidium bromide is a neurotoxin. Removal of both ethidium bromide and cesium chloride from the resulting band of plasmid DNA obtained by ultra-centrifugation was required before the DNA could be used in downstream processing techniques, such as sequencing, transfection, restriction analysis, or the polymerase chain reaction.

In recent years, many different matrices have been developed for use in the isolation of nucleic acids from complex biological materials. For example, matrices have been developed for the isolation of nucleic acids by ion-exchange chromatography (e.g., *J. of Chromatog.* 508:61–73 (1990); *Nucl. Acids Research* 21(12):2913–2915 (1993); U.S. Pat. No.'s 5,856,192; 5,82,988; 5,660,984; and 4,699,717), by reversed phase (e.g. Hirbayashi et al., *J of Chromatog.* 722:135–142 (1996); U.S. Pat. No. 5,057,426, by affinity chromatography (e.g., U.S. Pat. No. 5,712,383; and PolyATract® mRNA Purification System (Promega Corp., Madison, Wis.; see Promega's Technical Manual No. TM031), and by matricies which employ a combination of the above isolation modes (see, e.g. U.S. Pat. No. 5,652,348; *J. Chromatography* 270:117–126(1983))

One of the first solid phases developed for use in isolating nucleic acids was a specialized resin of porous silica gel particles designed for use in high performance liquid chromatography (HPLC). The surface of porous silica gel particles was functionalized with anion-exchangers which could exchange with plasmid DNA under certain salt and pH conditions. See, e.g. U.S. Pat. Nos.: 4,699,717, and 5,057,426. Machrey-Nagel Co. (Düren, Germany) was one of the first companies to provide HPLC columns packed with such anion-exchange silica gel particles, and it continues to sell such columns today. See, e.g. Information about NUCLEO-GEN® 4000-7DEAE in product information downloaded from the Machrey-Nagel homepage on the Internet on Jun. 12, 1998, at http://www.machrey-nagel.com. Each such column was designed so that plasmid DNA bound thereto is eluted in an aqueous solution containing a high concentration of a highly corrosive salt (e.g. plasmid DNA is eluted from the NUCLEOGEN® 4000-7DEAE column in 6 M urea). Each such column had to be washed thoroughly between each isolation procedure to remove the corrosive salt and contaminants bound to the column with the DNA from the system. The nucleic acid solution eluted therefrom also had to be processed further to remove the corrosive salt therefrom before it could be used in standard molecular biology techniques, such as cloning, transformation, digestion with restrictive enzymes, or amplification.

Various silica-based solid phase separation systems have been developed since the early HPLC systems described above. (See, e.g. the silica gel and glass mixture for isolating nucleic acids according to U.S. Pat. No. 5,658,548, and the porous support with silane bonded phase used to isolate oligonucleotides according to U.S. Pat. No. 4,767,670.) Modern silica-based systems utilize controlled pore glass, filters embedded with silica particles, silica gel particles, resins comprising silica in the form of diatomaceous earth, glass fibers or mixtures of the above. Each modern silica-based solid phase separation system is configured to reversibly bind nucleic acid materials when placed in contact with a medium containing such materials in the presence of chaotropic agents. Such solid phases are designed to remain bound to the nucleic acid material while the solid phase is exposed to an external force such as centrifugation or vacuum filtration to separate the matrix and nucleic acid material bound thereto from the remaining media components. The nucleic acid material is then eluted from the solid phase by exposing the solid phase to an elution solution, such as water or an elution buffer. Numerous commercial sources offer silica-based resins designed for use in centrifugation and/or filtration isolation systems. See, e.g. Wizard® DNA purification systems products from Promega Corporation (Madison, Wis., U.S.A.); or the QiaPrep® DNA isolation systems from Qiagen Corp. (Chatsworth, Calif., U.S.A.)

Magnetically responsive particles, formerly used to isolate and purify polypeptide molecules such as proteins or antibodies, have also been developed for use as solid phases in isolating nucleic acids. Several different types of magnetically responsive particles designed for isolation of such materials are described in the literature, and many of those types of particles are available from commercial sources. Such particles generally fall into either of two categories, those designed to reversibly bind nucleic acid materials directly, and those designed to reversibly bind nucleic acid materials through an intermediary. For an example of particles of the first type, see silica based porous particles designed to reversibly bind directly to DNA, such as MagneSil™ particles from Promega, or BioMag® magnetic particles from PerSeptive Biosystems. For examples of particles and systems of the second type designed to reversibly bind one particular type of nucleic acid (mRNA), see the PolyATract® Series 9600™ mRNA Isolation System from Promega Corporation (Madison, Wis., U.S.A.); or the ProActive® line of streptavidin coated microsphere particles from Bangs Laboratories (Carmel, Ind., U.S.A.). Both of these latter two systems employ magnetically responsive particles with avidin subunits covalently attached thereto, and streptavidin with an oligo dT moiety covalently attached thereto. The streptavidin-oligo dT molecules act as intermediaries, hybridizing to the poly A tail of mRNA molecules when placed into contact therewith, then binding to the particles through a releasable streptavidin-avidin bond.

The indirect binding magnetic separation systems for nucleic acid isolation or separation all require at least three components, i.e. magnetic particles, an intermediary, and a medium containing the nucleic acid material of interest. The intermediary/nucleic acid hybridization reaction and intermediary/particle binding reaction often require different solution and/or temperature reaction conditions from one another. Each additional component or solution used in the nucleic acid isolation procedure adds to the risk of contamination of the isolated end product by nucleases, metals, and other deleterious substances.

Various types of magnetically responsive silica based particles have been developed for use as solid phases in direct or indirect nucleic acid binding isolation methods. One such particle type is a magnetically responsive glass bead, preferably of a controlled pore size. See, e.g. Magnetic Porous Glass (MPG) particles from CPG, Inc. (Lincoln Park, N.J., U.S.A.); or porous magnetic glass particles described in U.S. Pat. Nos. 4,395,271; 4,233,169; or 4,297,337. Nucleic acid material tends to bind very tightly to glass, however, so that it can be difficult to remove once bound thereto. Therefore, elution efficiencies from magnetic glass particles tend to be low compared to elution efficiencies from particles containing lower amounts of a nucleic acid binding material such as silica.

Another type of magnetically responsive particle designed for use as a solid phase in direct binding and isolation of nucleic acids, particularly DNA, is a particle comprised of agarose embedded with smaller ferromagnetic particles and coated with glass. See, e.g. U.S. Pat. No. 5,395,498. A third type of magnetically responsive particle designed for direct binding and isolation of nucleic acids is produced by incorporating magnetic materials into the matrix of polymeric silicon dioxide compounds. See, e.g. German Patent No. DE 43 07 262 A1. The latter two types of magnetic particles, the agarose particle and the polymeric silicon dioxide matrix, tend to leach iron into a medium under the conditions required to bind nucleic acid materials directly to each such magnetic particle. It is also difficult to produce such particles with a sufficiently uniform and concentrated magnetic capacity to ensure rapid and efficient isolation of nucleic acid materials bound thereto.

Silica-based solid phase nucleic acid isolation systems, whether magnetic or non-magnetic based or configured for direct or indirect binding, are quick and easy to use and do not require the use of corrosive or hazardous chemicals. However, such are ineffective at isolating nucleic acids from contaminants, such as endotoxins, which tend to bind to and elute from such solid supports under the same conditions as nucleic acids. See, e.g. Cotten, Matt et al. *Gene Therapy* (1994) 1:239–246.

Some nucleic isolation systems have been developed in which a nucleic acid solution containing proteins is pre-treated with proteases to digest at least some of the proteins contained therein prior to isolation of the nucleic acid using a silica-based solid support of the type described above. See, e.g. QiaAmp™ Blood Kit provided by QIAGEN Inc. (Santa Clarita, Calif.), which utilizes protease; and Wizard® Plus SV Minipreps DNA Purification System provided by Promega Corp. (Madison, Wis.), which utilizes an alkaline protease. However, such pre-treatment systems require the introduction of one contaminant into a mixture to digest another contaminant. Carry-overproteases can limit the utility of nucleic acids isolated using such modified silica-based systems at least as much as nucleic acid samples contaminated with the proteins the proteases are introduced to digest. Specifically, given the proper solution conditions, proteases in a nucleic acid solution will digest any proteins introduced into the solution, including enzymes introduced therein to modify, cut, or transcribe the nucleic acid contained therein for downstream processing or analysis. Protease addition, incubation and removal steps also drive up the cost of nucleic acid isolation, costing time and money compared to isolation systems with no such additional steps.

In all the solid phase systems described above, each solid phase used therein has a substantially uniform surface composition designed to bind to a nucleic acid of interest, in the form of a silica or silica gel surface, or in the form of a silica gel or polymer surface modified with chemical groups exhibiting anion exchanger activities. Bimodal and multi-modal systems have also been developed, such as systems: (1) in which multiple columns each of which contains a solid phase modified with a different chemical group from the other columns in the system (e.g., Wheatley J. B., *J. Chromatogr.* (1992) 603: 273); (2) in which a single column is used with a single solid phase with at least two different chemical groups (e.g., Patent '680; Little, E. L. et al., *Anal. Chem.* (1991) 63: 33); or (3) in which two different solid phases are employed in the same column, wherein the two solid phases are separated from one another within the column by solid porous dividers (e.g., U.S. Pat. No. 5,660,984). Each of the chemical groups on the surface of the solid supports in the single column or multicolumn multimodal systems is configured to bind to different materials in whatever substrate is introduced into the system. Only a few such bimodal or multimodal column chromatography systems have been developed specifically for nucleic acid isolation (see, e.g. U.S. Pat. No. 5,316,680). Surface group combinations used in such solid phase systems include reverse phase, ion exchange, size exclusion, normal phase, hydrophobic interaction, hydrophilic interaction, and affinity chromatography. Such systems are designed such that only one of the surface groups binds a target species, such as a nucleic acid, while the other surface group(s) bind to and remove one or more non-target species in a mixture.

Bimodal and multimodal systems are far from simple, efficient alternatives to conventional organic or resin methods of nucleic acid isolation described above. Multi-column systems are inherently complex to run, as each column requires a unique set of mobile phase conditions to bind and/or release the desired target or non-target species bound to the stationary solid phase of the system. Non-target species tend to block adjacent functional groups configured to bind to the target species, thus adversely affecting overall yield. Also, all the bimodal or multimodal systems are only designed to separate a target species from other species for which functional groups have affinity.

At least one mixed mode ion exchange solid phase system has been developed for use in isolating certain types of target compounds, such as proteins or peptides, from an aqueous solution. See U.S. Pat. No. 5,652,348 (hereinafter, "Burton et al. '348") at col. 4, lines 21 to 25. The mixed mode ion exchange system of Burton et al. '348 comprises a solid support matrix with ionizable ligands covalently attached to the sold support matrix. The ionizable ligand is capable of exchanging with and adsorbing the target compound at a first pH and of releasing or desorbing the target compound at a second pH. The ionizable functionality is "either further electrostatically charged or charged at a different polarity at the second pH". (Burton et al. '348, claim 1, col. 25, lines 46–50). The examples of mixed mode ion exchange solid phase systems provided in the Burton et al. '348 patent contain only a single ionizable functionality, an amine residue capable of acting as an anion exchange group at the first pH. The concentration of ionizable ligands present on the solid support matrices disclosed in Burton et al. '348 is sufficiently high to "permit target protein binding at both high and low ionic strength". The only ligand density specifically disclosed and claimed as sufficiently high for the mixed mode ion exchange solid phase of Burton et al. '348 to bind to target proteins at high and low ionic strength is a ligand density which is "greater than the smaller of at least about 1 mmol/gram dryweight of resin or at least about 150 μmol/ml of resin" (col 13, lines 22–23; and claim 1). The mixed mode ion exchange system of Burton et al. '348, is specifically designed for use in the isolation of proteins and peptides, not nucleic acids or oligonucleotides.

Materials and methods are needed which can quickly, safely, and efficiently isolate target nucleic acids which are sufficiently free of contaminants to be used in molecular biology procedures. The present invention addresses the need for materials and methods which provide a rapid and efficient means for isolating target nucleic acids from any mixture of target nucleic acids and contaminants, including lysates of gram-negative bacteria, thereby providing purified nucleic acids which can be used in a variety of biological applications, including transfection of cultured cells and in vivo administration of nucleic acids to organisms.

BRIEF SUMMARY OF THE INVENTION

Briefly, in one aspect, the present invention is a pH dependent ion exchange matrix designed for use in isolating a target nucleic acid by adsorbing to the target nucleic acid at an adsorption pH and by releasing the target nucleic acid at a desorption pH which is higher than the adsorption pH.

In one embodiment of the present invention, the pH dependent ion exchange matrix comprises a solid support and a plurality of first ion exchange ligands, wherein each first ion exchange ligand comprises:

a cap comprising an amine with a pK of less than about 9, wherein the amine is selected from the group consisting of a primary, a secondary, or a tertiary amine;

a spacer covalently attached to the cap, the spacer comprising a spacer alkyl chain with an amine terminus, and an acidic moiety covalently attached to the spacer alkyl chain; and a linker comprising a linker alkyl chain covalently attached to the solid support at a first end of the linker alkyl chain and covalently attached to the amine terminus of the spacer at a second end of the linker alkyl chain.

In another embodiment, the present invention is a bimodal pH dependent ion exchange matrix having the same basic structure as the matrix described above except that the spacer does not include an acidic moiety, wherein the bimodal pH dependent ion exchange matrix further comprises a plurality of second ion exchange ligands covalently attached to the solid support. Each second ion exchange ligand comprises an alkyl chain with an acidic substituent covalently attached to the alkyl chain.

In another aspect, the present invention is a method of isolating a target nucleic acid using a pH dependent ion exchange matrix, according to steps comprising:

(a) providing the pH dependent ion exchange matrix;

(b) combining the matrix with a mixture comprising the target nucleic acid and at least one contaminant;

(c) incubating the matrix and mixture at an adsorption pH, wherein the target nucleic acid adsorbs to the matrix, forming a complex;

(d) separating the complex from the mixture; and (e) combining the complex with an elution solution at a desorption pH, wherein the target nucleic acid is desorbed from the complex.

In yet another aspect, the present invention is a method of making a pH dependent ion exchange matrix, comprising the steps of:

(a) providing a solid phase;

(b) providing a linker comprising a linker alkyl chain having a first end and a second end;

(c) combining the solid phase and the linker under conditions where a covalent bond is formed between the first end of the linker alkyl chain and the solid phase, thereby forming a linker-modified solid phase;

(d) providing an alkyl amine comprising:

a cap comprising an amine with a pK of less than about 9, wherein the amine is selected from the group consisting of a primary, secondary, or tertiary amine;

a spacer which is covalently attached to the cap, wherein the spacer comprises a spacer alkyl chain with an amino terminus, and an acidic substituent covalently attached to the spacer alkyl chain; and (e) combining the linker-modified solid phase with the alkyl amine under conditions where a covalent bond is formed between the amino terminus of the spacer alkyl chain and the second end of the linker.

In yet another embodiment, the present invention is a method of making a pH dependent ion exchange matrix, according to the steps comprising:

(a) providing a solid support;
(b) providing a first ion exchange ligand comprising:
   a cap comprising an amine with a pK of less than about 9, wherein the amine is selected from the group consisting of a primary, secondary, or tertiary amine;
   a spacer covalently attached to the cap, the spacer comprising a spacer alkyl chain with an amine terminus, an acidic substitutent covalently attached to the spacer alkyl chain, and a protecting group covalently attached to the acidic substituent; and
   a linker comprising a linker alkyl chain having a first end and a second end, wherein the second end is covalently attached to the amine terminus of the spacer;
(c) combining the solid phase and the first ion exchange ligand under conditions where a covalent bond is formed between solid phase and the first end of the linker alkyl chain; and
(d) deprotecting the acidic substituent of the first ligand.

Another embodiment of the present invention is a method of making a bimodal pH dependent ion exchange matrix according to the steps comprising:

(a) providing a solid support;
(b) providing a first ion exchange ligand comprising:
   a cap comprising an amine having a pK of less than about 9, wherein the amine is selected from the group consisting of a primary, secondary, or tertiary amine;
   a spacer covalently attached to the cap, the spacer comprising a spacer alkyl chain with an amine terminus; and
   a linker comprising a linker alkyl chain having a first end and a second end, wherein the second end is covalently attached to the amine terminus of the spacer; and
(c) combining the solid phase and the first ion exchange ligand under conditions where a covalent bond is formed between solid phase and the first end of the linker alkyl chain.
(d) combining the first ion exchange-modified solid phase with a second ion exchange ligand under conditions where a covalent bond is formed between the solid phase and one end of the second ion exchange ligand, wherein the ion exchange ligand comprises a second alkyl chain, an acidic substituent covalently attached to the second alkyl chain, and a protecting group attached to the acidic substitutent.
(e) removing the protecting group from the acidic substituent.

The methods and materials of the present invention can be used to isolate target nucleic acids including, but not limited to plasmid DNA, total RNA, amplified nucleic acids, and genomic DNA from a variety of contaminants, including but not limited to agarose and components of a bacteria, animal tissue, blood cells, and non-target nucleic acids.

Applications of the methods and compositions of the present invention to isolate nucleic acids from a variety of different media will become apparent from the detailed description of the invention below. Those skilled in the art of this invention will appreciate that the detailed description of the invention is meant to be exemplary only and should not be viewed as limiting the scope of the invention.

DETAILED DESCRIPTION OF THE INVENTION

Figure 1:
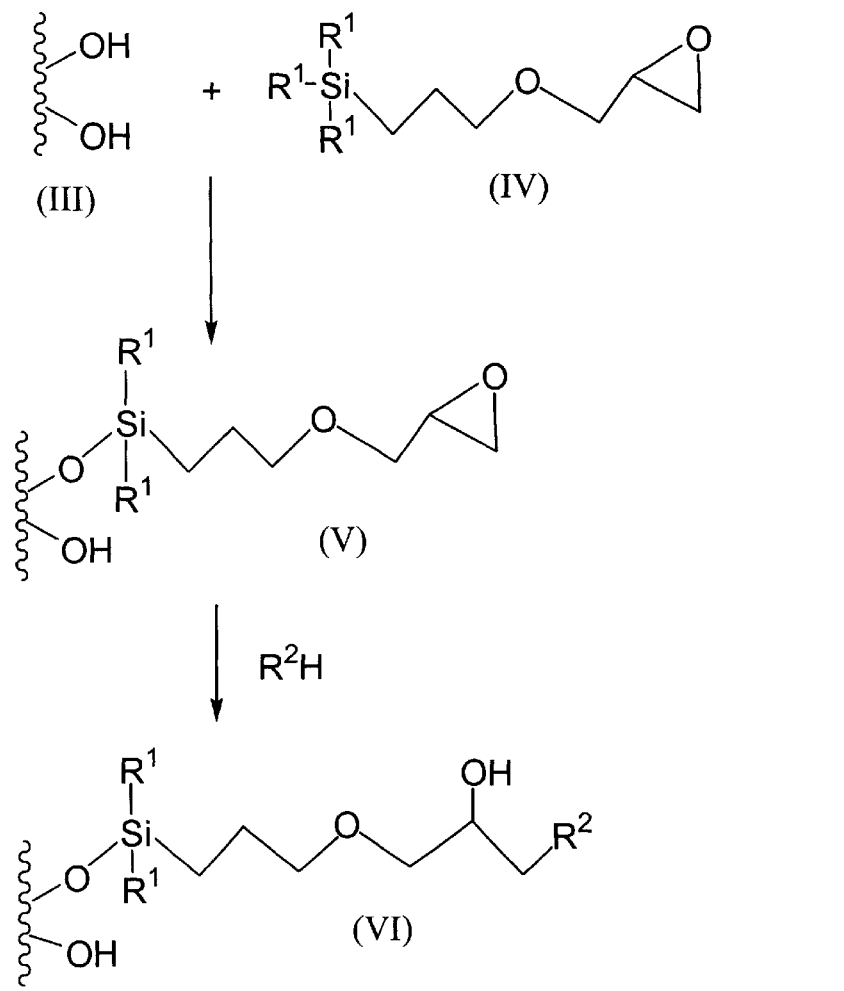
FIG. 1 illustrates a method of making a pH dependent ion exchange matrix wherein a cap, comprising an amine with a pK of less than about 9, is covalently attached to a solid phase through a glycidyl linker.
Figure 1:
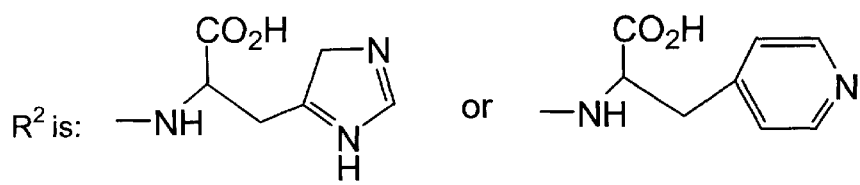
Figure 1:
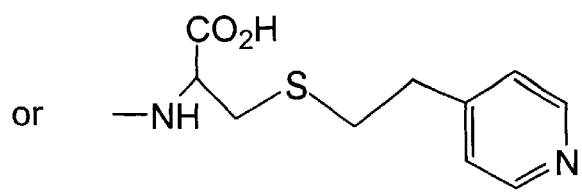

The term "alkyl chain" as used herein refers to a straight chain alkane optionally substituted with at least one oxygen, nitrogen, or sulfur atom.

The term "pH dependent ion exchange matrix", as used herein, refers to a matrix of a solid support and a plurality of ligands covalently attached thereto wherein at least one ligand includes an acidic moiety, and the same or a different ligand covalently attached to the same matrix comprises an amine with a pK of less than about 9, wherein the matrix has a capacity to adsorb to a target nucleic acid at a first pH and to desorb the target nucleic acid at a desorption pH which is higher than the first pH.

The term "solid phase" is used herein in a standard chromatographic sense, to refer to an insoluble, usually rigid, matrix or stationary phase which interacts with a solute, in this case a target nucleic acid, in a solute mixture. The term solid phase, as used herein, specifically includes stationary phases in liquid chromatography (LC), high pressure liquid chromatography (HPLC), particulate matrices embedded into or bound to filters, and magnetic or non-magnetic porous matrix particles which interact with solutes when added directly to a solute mixture.

The term "silica gel" as used herein refers to chromatography grade silica gel, a substance which is commercially available from a number of different sources. Silica gel is most commonly prepared by acidifying a solution containing silicate, e.g. by acidifying sodium silicate to a pH of less than 11, and then allowing the acidified solution to gel. See, e.g. silica preparation discussion in *Kurt-Othmer Encyclopedia of Chemical Technology*, Vol. 21, 4th ed., Mary Howe-Grant, ed., John Wiley & Sons, pub., 1997, p. 1021.

The term "glass particles" as used herein means particles of crystalline or vitreous silicas, even though crystalline silicas are not formally "glasses" because they are not amorphous, or particles of glass made primarily of silica. The term includes quartz, vitreous silica, controlled pore glass particles, and glass fibers.

As used herein, the term "silica magnetic particles" refers to silica based solid phases which are further comprised of materials which have no magnetic field but which form a magnetic dipole when exposed to a magnetic field, i.e., materials capable of being magnetized in the presence of a magnetic field but which are not themselves magnetic in the absence of such a field.

The term "magnetic" as used to refer to silica magnetic particles includes materials which are paramagnetic or superparamagnetic materials. The term "magnetic", as used herein, also encompasses temporarily magnetic materials, such as ferromagnetic or ferromagnetic materials. Except where indicated otherwise below, the silica magnetic particles used in this invention preferably comprise a superparamagnetic core coated with siliceous oxide, having a hydrous siliceous oxide adsorptive surface (i.e. a surface characterized by the presence of silanol groups).

The term "surface", as used herein, refers to the portion of the support material of a solid phase which comes into direct contact with a solution when the solid phase is combined therewith.

The term "nucleic acid" as used herein refers to any DNA or RNA molecule or a DNA/RNA hybrid molecule. The term includes plasmid DNA, amplified DNA or RNA fragments, total RNA, mRNA, and genomic DNA.

The term "target nucleic acid" as used herein refers to the particular species of nucleic acid to be isolated in any particular application of the methods or use of the pH dependent ion exchange matrix of the present invention. The target nucleic acid is preferably at least 20 nucleotides long, more preferably at least 100 nucleotides long, and most preferably at least 1,000 nucleotides long.

The solid support component of the pH dependent ion exchange matrix can be made of any common support material, including soft gel supports such as agarose, polyacrylamide, or cellulose, or hard support material such as polystyrene, latex methacrylate, or silica. When the solid phase support material is silica, it is preferably in the form of silica gel, siliceous oxide, solid silica such as glass or diatomaceous earth, or a mixture of two or more of the above. Silica based solid phases suitable for use in the pH dependent ion exchange matrixes of the present invention include the mixture of silica gel and glass described in U.S. Pat. No. 5,658,548, the silicamagnetic particles described in PCT Publication Number WO 98/31840, and solid phases sold by Promega Corporation for use in plasmid DNA isolation, i.e. Wizard® Minipreps DNA Purification Resin. Silica gel particles are particularly preferred for use as the solid phase in the pH dependent ion exchange matrix and methods of the present invention. Silica gel particles are stable at much higher pressures than solid phases made from soft gel support material, making the silica gel solid phases suitable for HPLC as well as LC and batch separation applications.

The pH dependent ion exchange matrix used in the present invention is preferably in a form which can be separated from a solute mixture comprising the target nucleic acid and at least one contaminant after the solute mixture is combined therewith, by application of an external force. A skilled artisan would appreciate that the type of external force suitable for use in separating the matrix from the solute mix depends upon the form in which the matrix is presented to the solute mix, and upon the physical properties of the matrix itself. For example, gravity can be used to separate the pH dependent ion exchange matrix from the solute mix when the matrix is in the form of a chromatographic resin loaded on an LC column, when the matrix is in the form of silica particles (e.g., controlled pore glass, silica gel particles, or silica magnetic particles) which are added batch-wise to a solute mixture and then separated therefrom by decantation or filtration, or when the mixed-mode matrix is in the form of a filter with silica particles or chromatographic resin embedded into or attached thereto.

The external force used in the method of isolation is high pressure liquid when the pH dependent ion exchange matrix is the stationary phase of a high pressure liquid chromatography column (HPLC). Other forms of external force suitable for use in the method of this invention include vacuum filtration (e.g. when the solid phase component of the matrix is particles of controlled pore glass, particles of silica gel or silica magnetic particles, or mixtures of one or more of the above types of particles embedded into or attached to a filter), centrifugation (e.g. when the mixed-bed solid phase is particulate), or magnetic (e.g. when the mixed-bed solid phase comprises magnetic or paramagnetic particles).

When the solid phase component of the pH dependent ion exchange matrix is a silica gel particle, it is most preferably a silica magnetic particle. A silica magnetic particle can be separated from a solution using any of the external means described above for use with other types of solid phases, such as those described above. However, unlike the other solid phases, a silica magnetic particle can be separated from a solution by magnetic force, a quick and efficient means of separating a matrix from a solution.

When the solid support component of the pH dependent ion exchange matrix is a silica magnetic particle, the size of the particle is preferably selected as follows. Smaller silica magnetic particles provide more surface area (on a per weight unit basis) for covalent attachment to the plurality of ion exchange ligands, but smaller particles are limited in the amount of magnetic material which can be incorporated into such particles compared to larger particles. The median particle size of the silica magnetic particles used in a particularly preferred embodiment of the present invention is about 1 to 15 $\mu$m, more preferably about 3 to 10 $\mu$m, and most preferably about 4 to 7 $\mu$m. The particle size distribution may also be varied. However, a relatively narrow monodal particle size distribution is preferred. The monodal particle size distribution is preferably such that about 80% by weight of the particles are within a 10 $\mu$m range of the median particle size, more preferably within an 8 $\mu$m range, and most preferably within a 6 $\mu$m range.

The solid support component of the pH dependent ion exchange matrix can be porous or non-porous. When the solid support is porous, the pores are preferably of a controlled size range sufficiently large to admit the target nucleic acid material into the interior of the solid phase particle, and to bind to functional groups or silica on the interior surface of the pores. The total pore volume of a silica magnetic particle, as measured by nitrogen BET method, is preferably at least about 0.2 ml/g of particle mass. The total pore volume of porous silica magnetic particles particularly preferred for use as components of the pH dependent ion exchange matrix of the present invention, as measured by nitrogen BET, is preferably at least about 50% of the pore volume is contained in pores having a diameter of 600 Å or greater.

Silica magnetic particles may contain substances, such as transition metals or volatile organics, which could adversely affect the utility of target nucleic acids substantially contaminated with such substances. Specifically, such contaminants could affect downstream processing, analysis, and/or use of the such materials, for example, by inhibiting enzyme activity or nicking or degrading the target nucleic acids isolated therewith. Any such substances present in the silica magnetic particles used in the present invention are preferably present in a form which does not readily leach out of the particle and into the isolated biological target material produced according to the methods of the present invention. Iron is one such undesirable at least one contaminant, particularly when the biological target material is a target nucleic acid.

Iron, in the form of magnetite, is present at the core of particularly preferred forms of silica magnetic particles used as the solid phase component of the pH dependent ion exchange matrixes of the present invention. Iron has a broad absorption peak between 260 and 270 nanometers (nm). Target nucleic acids have a peak absorption at about 260 nm, so iron contamination in a target nucleic acid sample can adversely affect the accuracy of the results of quantitative spectrophotometric analysis of such samples. Any iron containing silica magnetic particles used to isolate target nucleic acids using the present invention preferably do not produce isolated target nucleic acid material sufficiently contaminated with iron for the iron to interfere with spectrophotometric analysis of the material at or around 260 nm.

The most preferred silica magnetic particles used in the matrixes and methods of the present invention, siliceous oxide coated silica magnetic particles, leach no more than 50 ppm, more preferably no more than 10 ppm, and most preferably no more than 5 ppm of transition metals when assayed as follows. Specifically, the particles are assayed as follows: 0.33 g of the particles (oven dried @ 110° C.) are combined with 20 ml. of 1N HCl aqueous solution (using deionized water). The resulting mixture is then agitated only to disperse the particles. After about 15 minutes total contact time, a portion of the liquid from the mixture is then analyzed for metals content. Any conventional elemental analysis technique may be employed to quantify the amount of transition metal in the resulting liquid, but inductively coupled plasma spectroscopy (ICP) is preferred.

At least two commercial silica magnetic particles are particularly preferred for use in the matrix of the present invention, BioMag® Magnetic Particles from PerSeptive Biosystems, and the MagneSil™ Particles available from Promega Corporation (Madison, Wis.). Any source of magnetic force sufficiently strong to separate the silica magnetic particles from a solution would be suitable for use in the nucleic acid isolation methods of the present invention. However, the magnetic force is preferably provided in the form of a magnetic separation stand, such as one of the MagneSphere® Technology Magnetic Separation Stands (cat. no.'s Z5331 to 3, or Z5341 to 3) from Promega Corporation.

The pH dependent ion exchange matrices of the present invention all include a plurality of first ion exchange ligands covalently attached to a solid phase, according the general structure of formula (1), below:

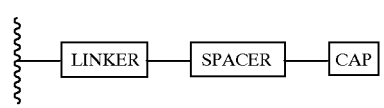

(I)

wherein the wavy line represents a surface of the solid phase. LINKER comprises a linker alkyl chain, preferably an alkyl chain which includes three (3) to eight (8) carbon atoms. The LINKER preferably also includes at least one additional member selected from the group consisting of oxygen, amine, and carbonyl. The LINKER is preferably an epoxide, such as a glycidyl moiety, or a urea linkage. The SPACER comprises a spacer alkyl chain with an amine terminus, wherein the amine terminus is covalently attached to the LINKER. The other end of the spacer alkyl chain is covalently attached to the CAP. The SPACER alkyl chain can be substituted by at least one sulphur residue. The CAP comprises a primary, secondary, or tertiary amine with a pK value less than 9. The CAP preferably further comprises an aromatic hydrocarbon ring, wherein the amine is either attached to or a member of the ring. When the CAP comprises an aromatic hydrocarbon ring and an amine, the amine is preferably a member of the ring. The CAP more preferably comprises a five or six member aromatic amine ring, such as imidazole or pyridine.

In one embodiment of the present invention, wherein the plurality of first ion exchange ligands are the only ion exchange ligands attached to the solid phase, the SPACER further comprises a first acidic moiety covalently attached to the spacer alkyl chain. The acidic moiety is preferably a carboxyl residue. In this embodiment of the invention, at least one basic (the amine member of the aromatic hydrocarbon) and at least one acidic moiety are both members of the first ligand. The SPACER is preferably selected from the group consisting of cysteine, alanine, and the alkyl chain portion of a polar amino acid consisting of an alkyl chain and an aromatic hydrocarbon such as histamine and histidine. SPACER and CAP together most preferably define a histamine or a histidine moiety.

In another embodiment, the present invention is a pH dependent ion exchange matrix comprising a plurality of first ion exchange ligands and a plurality of second ion exchange ligands covalently attached to the same solid support, such as the same silica magnetic particle. The second ion exchange ligand comprises a second alkyl chain and an ion exchange residue covalently attached thereto. The second alkyl chain is preferably an unbranched alkane of one (1) to five (5) carbon atoms. The ion exchange residue is preferably an acidic moiety, more preferably a carboxylic acid. The second ion exchange ligand is most preferably propionate.

In this second embodiment of the pH dependent ion exchange matrix, each first ion exchange ligand can have the same structure as set forth in Formula (I), above, except that the first ion exchange ligand need not have an acidic moiety covalently attached to the spacer alkyl chain when the second ion exchange ligand includes such a moiety. When the second ion exchange ligand includes an acidic moiety, it is preferably a carboxylic acid residue, more preferably a carboxylic acid residue covalently attached to the terminus of the second alkyl chain.

The second type of pH ion exchange matrix described immediately above, hereinafter the "bimodal" ion exchange matrix, preferably has an acidic moiety on one ligand, the second ion exchange ligand, and at least one basic moiety on the other ligand, the amine member of the aromatic hydrocarbon ring component of the first ion exchange ligand. In that preferred configuration, target nucleic acid binding and release capacity of the matrix can be controlled and even fine tuned by varying the relative proportion of first and second ion exchange ligands covalently bound to the solid support. This feature of the bimodal ion exchange matrix makes it particularly desirable for use in the methods of the present invention, although the monomodal ion exchange matrix described above is also well suited for use in the isolation of target nucleic acids according to the present methods. When the solid phase is silica based, each ion exchange ligand is preferably covalently attached to the solid phase through a silane group, as shown in formula (II), below:

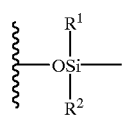

(II)

Wherein, $R^1$ is selected from the group consisting of —OH, —OCH$_3$, and —OCH$_2$CH$_3$; and $R^2$ is represented by the formula —(OSiR$^1{}_2$)$_y$—R$^1$, wherein y is at least 0. When y is zero (0), the ligand is connected to the solid support through a silane monomer. When y is greater than zero, the connection is through a silane polymer.

Target nucleic acids are inherently negatively charged at any pH higher than 2, and can, therefore, reversibly bind to anion-exchangers under solution conditions where ions can be exchanged between the anion-exchanger and the target nucleic acid. The pH dependent ion exchange matrix of the present invention is an anion exchanger at a first pH in which the matrix present is neutral to positively charged. At a second, higher pH the matrix becomes neutral to negatively charged depending on the pK of the acidic moiety of the ion exchange ligand. The target nucleic acid can adsorb to the matrix at the first pH and desorb from the matrix at the second pH. The possible pH range for each of the first and second pH depends upon the nature of the plurality of ion exchange ligands component of the pH dependent ion exchange matrix.

The plurality of ligands include at least one anion-exchange moiety and at least one cation-exchange moiety. The at least one anion-exchange moiety of the pH dependent ion exchange matrix is at least one amine with a pK of less than 9, wherein the amine is selected from the group consisting of a primary, secondary, or tertiary amine. The at least one cation-exchange moiety is an acidic moiety, preferably selected from the group consisting of hydroxyl and carboxyl.

The pH dependent ion exchange solid phase of the present invention is designed for use in the isolation of target nucleic acids. Both the ligand configuration, described above, and ligand density can be adjusted to ensure optimal adsorption and desorption of a given target nucleic acid. The highest ligand density suitable for use in the matrices of the present invention is 500 μmol per gram of dry weight. The lowest ligand density suitable for use in the pH dependent ion exchange matrices of the present invention is about 25 μmol/g dry weight. The ligand density in the matrices of the present invention is most preferably between 50 and 200 μmol/g dry weight of solid phase.

The anion exchange moiety and cation exchange moiety of the present matrix vary in charge depending upon solution conditions. In the presence of a solution having a first pH, the basic moiety (i.e., the amine) is positively charged and the matrix is capable of exchanging with the target nucleic acid. In the presence of a solution having a second pH which is higher than the first pH, the acidic moiety has a negative charge and the basic moiety has a neutral charge. The matrix is designed to adsorb the target nucleic acid at the first pH and to desorb the target nucleic acid at a pH which is at least about the second pH. pH conditions necessary to ensure adsorption and desorption of the target nucleic acid to the matrix of the present invention depend upon the salt conditions of the adsorption and desorption solutions, and upon the specific composition and density of the plurality of ligands attached to the solid phase. Specifically, the first pH, at which desorption takes place, is preferably between pH 6 and 8 when the ionic strength of the solution is preferably no higher than about 1 M salt, more preferably no higher than about 500 mM salt, and most preferably no higher than about 50 mM salt.

The method of isolating a target nucleic acid of the present invention can employ either type of pH dependent ion exchange matrix of the present invention described above alone, or a mixed bed of a pH dependent ion exchange matrix and another type of matrix capable of binding and releasing the target nucleic acid under a different set of solution conditions such as is described in the concurrently filed U.S. patent application Ser. No. 09/312,139 for MIXED BED SOLID PHASE AND ITS USE IN THE ISOLATION OF NUCLEIC ACIDS.

The present method comprises the steps of providing the pH dependent ion exchange matrix to be used in the method, providing a mixture comprising the target nucleic acid and at least one contaminant, combining the mixture and the matrix at a first pH under conditions where the target nucleic acid adsorbs to the matrix to form a complex, separating the complex from the mixture, and desorbing the target nucleic acid from the complex by combining the complex with an elution solution at a desorption pH. The exact solution conditions necessary to ensure adsorption and desorption of the target nucleic acid to the matrix vary depending upon several factors, including the nature of the target nucleic acid (e.g., RNA or DNA, molecular weight, and nucleotide sequence composition), the pKa and pKb of the acidic and basic subunits of the ligands, ligand density on the surface of a solid phase, and capacity of the solid phase to bind directly to the target nucleic acid. Some contaminants in the mixture can also interfere with adherence to the matrix.

Preferably, no chaotropic agent (e.g. guanidine hydrochloride or guanidine isothiocyanate) or low molecular weight alcohol (e.g. ethanol or methanol) is included in any of the solutions which come into contact with the matrix regardless of the particular species of target nucleic acid. Even trace amounts of chaotropic agents or ethanol in a solution of target nucleic acid can severely limit the utility of the nucleic acid in downstream processing or analysis.

When the target nucleic acid is plasmid DNA, the pH dependent ion exchange matrix of the present invention can be added directly to the cleared lysate of bacteria transformed with the plasmid DNA and lysed with an alkaline lysis solution. Alkaline lysis procedures suitable for use in the present invention can be found in Sambrook et al, Molecular Cloning, Vol. 1, 2$^{nd}$ ed. (pub. 1989 by Cold Spring Harbor Laboratory Press), pp. 1.25–1.28, and in Technical Bulletin No's 202, 225, and 259 (Promega Corp.). Plasmid DNA from a lysate solution prepared as described above will adsorb to the pH dependent ion exchange matrix upon combination therewith, provided the overall charge of the matrix is positive, and provided the charge density is sufficiently high to enable to plasmid DNA to participate in anion exchange with the ion exchange ligands of the matrix at a first pH. Once adsorbed to the matrix to form a complex, the complex can be washed in a wash solution with buffer and salt solution conditions designed to ensure the plasmid DNA remains adsorbed to the matrix throughout any such washing steps, while removing at least one contaminant. Finally, the plasmid DNA is eluted from the complex by combining the complex with an elution buffer having a second pH above that of the lysate and wash solutions, wherein the second pH is sufficiently high to promote desorption of the plasmid DNA from the matrix.

The pH dependent ion exchange matrix and methods of the present invention can be used to isolate genomic DNA from living tissue, including but not limited to blood, semen, vaginal cells, hair, buccal tissue, saliva, tissue culture cells, plant cells, placental cells, or fetal cells present in amniotic fluid and mixtures of body fluids. When the target nucleic acid is genomic DNA, it is necessary to disrupt the tissue to release the target genomic DNA from association with other material in the tissue, so the target genomic DNA can adhere to the pH dependent ion exchange matrix in the presence of a solution at the first pH. The resulting complex of matrix and genomic DNA is separated from the disrupted tissue, and washed to remove additional contaminants (if necessary). The genomic DNA is then eluted from the complex by combining the complex with an elution solution having a second pH which is higher than the first pH.

When the target nucleic acid is RNA, adsorption of the target nucleic acid to the pH dependent ion exchange matrix is preferably carried out under conditions designed to promote preferential adsorption of RNA to the matrix. When both RNA and DNA are present in a solution, the solution conditions can be designed to promote preferential adsorption of RNA to the pH dependent ion exchange matrix. The specific solution conditions required to preferentially promote adsorption and desorption of RNA to a pH dependent ion exchange matrix will depend upon the characteristics of the matrix itself, and must therefore be determined for each matrix.

Figure 2:
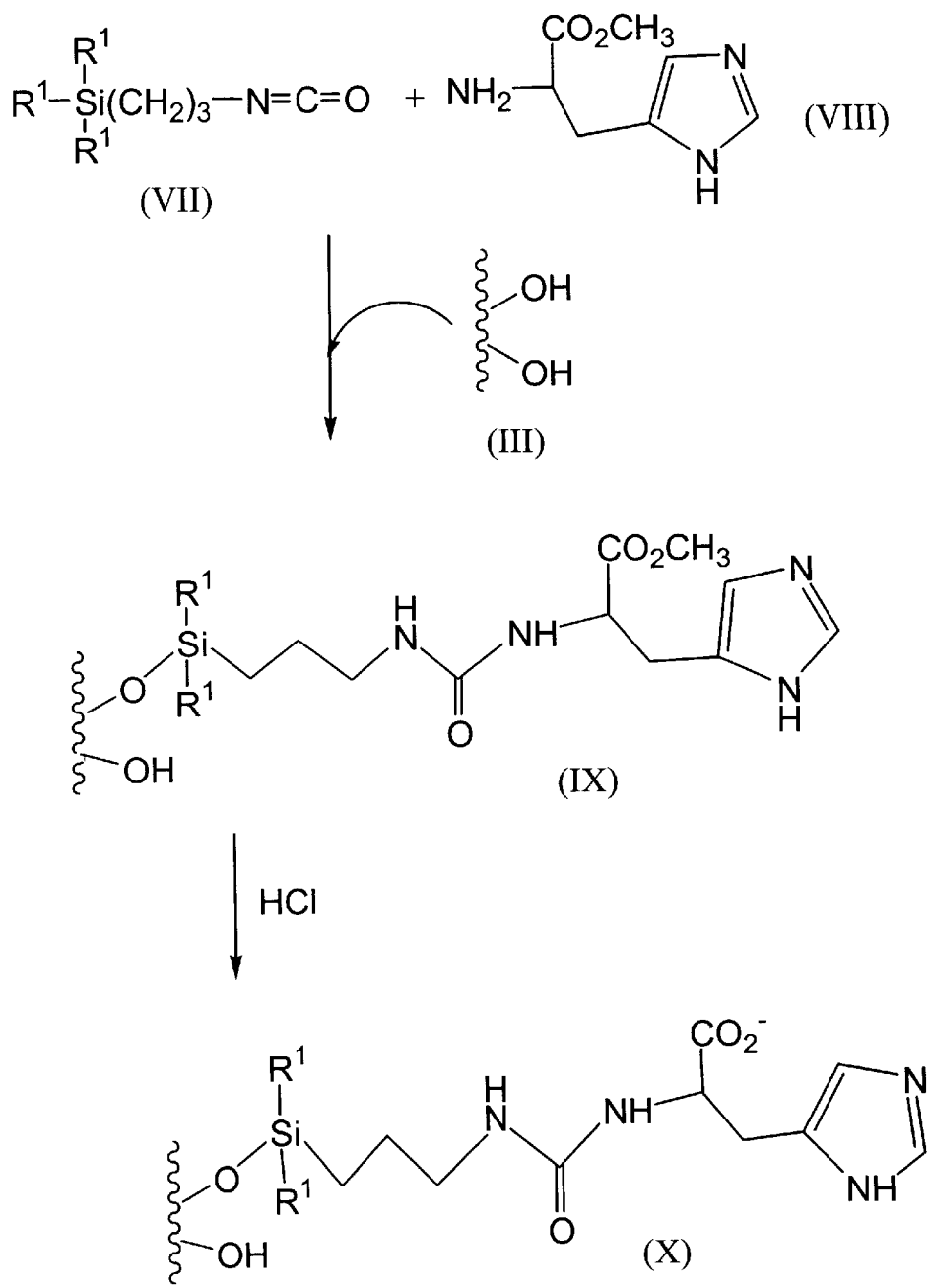
FIG. 2 illustrates a method of making a pH dependent ion exchange matrix by linking an amino alkyl spacer and a cap comprising an aromatic hydrocarbon ring with an amine member, to a sold phase through a urea linkage.
Figure 3:
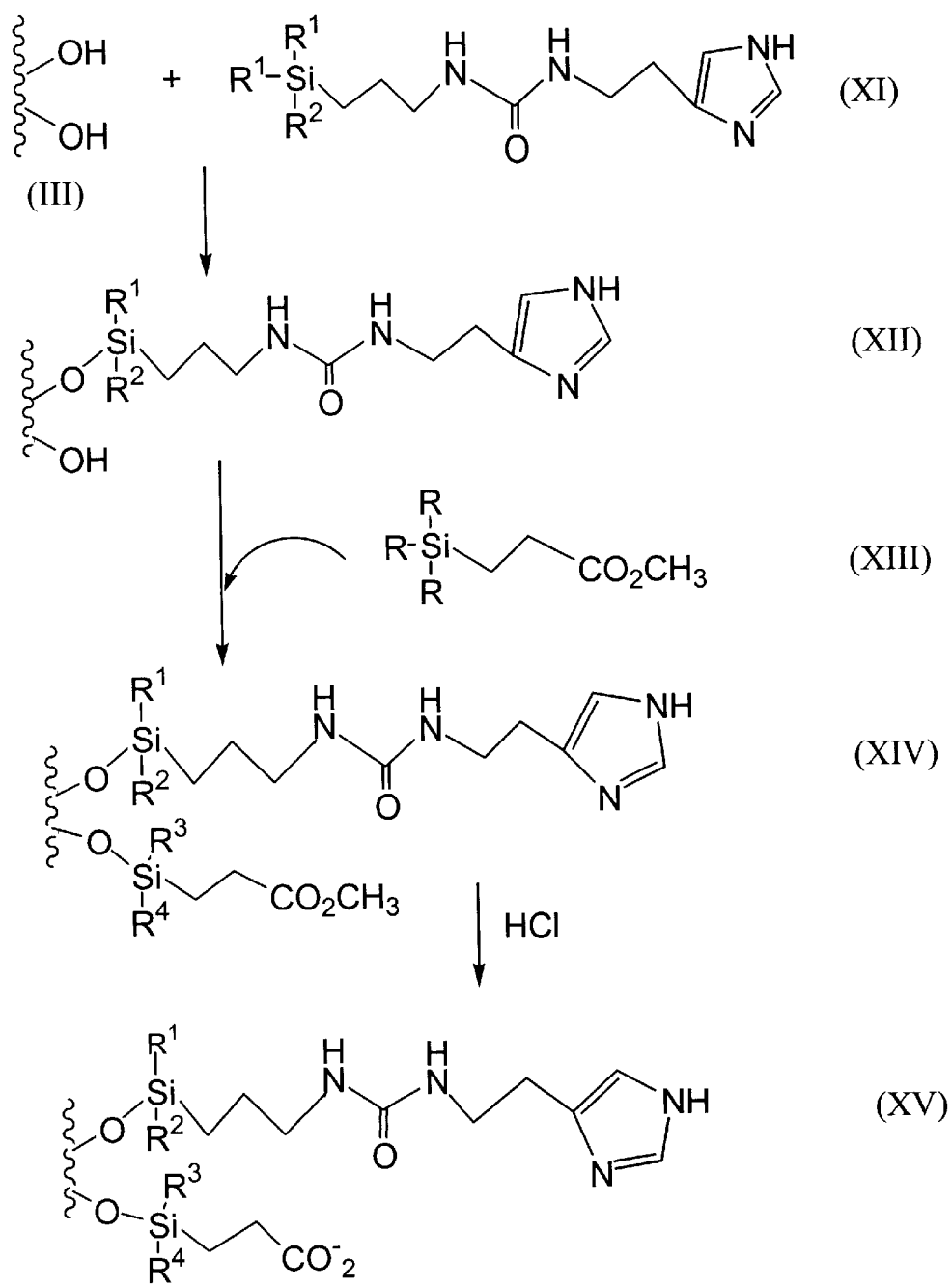
FIG. 3 illustrates a method of making a bimodal pH dependent ion exchange matrix.

FIGS. 1 through 3 illustrate three additional embodiments of the present invention, specifically, three different methods of making three different types of pH dependent ion exchange matrices. The first such method, one illustrated in FIG. 1, is a method of making a pH dependent ion exchange matrix by linking a cap, comprising of an aromatic hydrocarbon ring with an amine member, wherein the amine has a pK of less than about 9, to a solid phase through a glycidyl linker. The method comprises three steps. In the first step, the compound of formula (IV), a glycidypropylsilane with three identical subunits ("$R^1$", which is —OH, —$OCH_3$, or —$OCH_2CH_3$) covalently attached to the silane residue, is combined with a solid phase with at least one surface as shown in formula (III), with hydroxyl groups covalently attached thereto, under conditions designed to promote the formation of a covalent bond between the silane residue, forming the glycidyl-modified solid phase of formula (V). Finally, the glycidyl modified solid phase is combined with either an amino acid which includes an amino acid with an aromatic hydrocarbon ring with an amine member, such as histidine, or a amino acid covalently attached to an aromatic hydrocarbon, such as pyridyl-cysteine or pyridyl-alanine, under conditions designed to promote formation of a peptide bond between the two compounds through the N-terminus of the amino acid or amino acid moiety. Preferred compounds used in this particular step of the method are represented as $R^2H$, wherein the structures for the $R^2$ component of each such compound (i.e., histidine, pyridyl-cysteine, and pyridyl-alanine), are illustrated in FIG. 1. The end product of this reaction is the pH dependent ion exchange matrix of formula (VI).

The present invention is also a method of making a pH dependent ion exchange matrix by linking a first moiety, comprising an amino alkyl spacer and a cap comprising an aromatic hydrocarbon ring with an amine member, to a solid phase through a urea linkage. FIG. 2 illustrates such a method of synthesis wherein histidine is the first moiety linked to the solid phase. However, it is contemplated that substantially the same procedure could be used to link other moieties to solid phases through urea, including histamine. As illustrated in FIG. 2, histidine modified by protection of the carboxyl residue with a methyl group, according to formula (VII), is combined with the compound of formula (VIII), a 3-isocyanto propylsilane with three identical subunits ("$R^1$'", which is —OH, —$OCH_3$, or —$OCH_2CH_3$) covalently attached to the silane residue. The resulting mixture is allowed to react under conditions which promote formation of a covalent bond between the N-terminus of the protected amino acid (histidine protected by a methyl group, in this case) and the cyanato carbon residue of the compound of formula (VIII), resulting in the formation of a urea residue. The product of the first reaction is then combined with the solid phase of formula (III) under conditions designed to promote formation of a covalent bond between the silane residue of the product and the hydroxyl groups at a surface of the solid phase. The end product of the second reaction is represented by formula (IX). Finally, the protecting group on the carboxylic acid residue of the amino acid moiety is removed by reaction with an oxidant, such as hydrochloric acid. The product of the reaction is represented by formula (X).

The present invention is also a method of making a bimodal or multimodal pH dependent ion exchange matrix. FIG. 3 illustrates the synthesis of one such bimodal matrix, according to the method of the present invention. The first step of the method shown in FIG. 3 is the addition of the compound of formula (XI), an imidazole-ethyl-N'-3-propylsilyurea wherein three subunits, two $R^1$ subunits each defined as —OH, —$OCH_3$, or —$OCH_2CH_3$ and one $R^2$ subunit, defined by the formula —$(OSiR^1_2)_y$—$R^1$ wherein y is at least 0. covalently attached to the silane residue, to a solid phase with hydroxyl groups covalently attached thereto, as shown in formula (III). The compound of formula (XI) can be synthesized from histidine and 3-isocyanatopropyltri-substituted silane, using a similar procedure to that used to form the urea linkage in the first step of the method discussed immediately above. The compound of formula (XI) and the solid phase of formula (III) are allowed to react under conditions designed to promote formation of a covalent bond between the silane residue of the compound of formula (XI) and the hydroxyl groups at the surface of the solid phase, thereby forming the solid phase with a first type of linker attached thereto, the structure of formula (XII).

The synthesis of the bimodal and multimodal pH dependent ion exchange matricies, continues with the addition of at least one other linker. In a bimodal matrix, the at least one other linker is a second linker which includes an acidic group covalently attached thereto. Attachment of a second linker to the structure of formula (XII) according to the present method is illustrated in FIG. 3. An alkyl chain with a protected acidic group covalently attached thereto and a terminal silane residue with three identical subunits ("$R^3$", which is —OH, —$OCH_3$, or —$OCH_2CH_3$) covalently attached to the silane residue, such as the compound of formula (XIII), is combined with the solid phase/first linker compound of formula (XII) under conditions which promote the formation of a covalent bond between the silane residue and the hydroxyl groups at a surface of the solid phase. The protecting group (e.g., a methyl residue) is then removed from the resulting compound of formula (XIV), using an oxidant such as HCl, thereby forming the compound of formula (XV). The silane residue of both the intermediate compound formula (XIV) and the end product of formula (XV) has two subunits attached thereto, $R^3$ and $R^4$, wherein R3 is —OH, —$OCH_3$, or —$OCH_2CH_3$, and $R^4$ is —$(OSiR^3_2)_z$—$R^3$, wherein z is at least 0.

Multimodal pH dependent ion exchange matrices can also be made, by covalently attaching additional linkers with acidic or basic residues to a solid phase to fine tune the charge density and overall charge of a solid phase to select for particular target nucleic acids.

The following, non-limiting examples teach various embodiments of the invention. In the examples, and elsewhere in the specification and claims, volumes and concentrations are at room temperature unless specified otherwise. The magnetic silica particles used in the examples below were all either porous or nonporous MagneSil™ particles having the general preferred dimensions and siliceous oxide coating described as preferred above.

More specifically, the porous MagneSil™ particles used in the Examples below were taken from either of two batches of particles having the following characteristics: (1) a surface area of 55 m²/g, pore volume of 0.181 ml/g for particles of <600 Å diameter, pore volume of 0.163 ml/g for particles of >600 Å diameter, median particle size of 5.3 μm, and iron leach of 2.8 ppm when assayed as described herein above using ICP; or (2) a surface area of 49 m²/g, pore volume of 0.160 ml/g (<600 Å diameter), pore volume of 0.163 ml/g (>600 Å diameter), median particle size of 5.5μm, and iron leach of 2.0 ppm. Specifications of glass particles used in the examples below are provided below.

One skilled in the art of the present invention will be able to use the teachings of the present disclosure to select and use solid supports other than the three silica based solid supports used to make the pH dependent ion exchange particles whose synthesis and use is illustrated in the Examples below. The Examples should not be construed as limiting the scope of the present invention. Other pH dependent ion exchange matrixes, and methods of using the matrixes to isolate target material according to the present invention will be apparent to those skilled in the art of chromatographic separations and molecular biology.

EXAMPLES

The following examples are given to illustrate various aspects of the invention, without limiting the scope thereof:

Example 1

Gel Electrophoresis

Samples of target nucleic acids isolated according to procedures described in Examples below were analyzed for contamination with non-target nucleic acids, and for size as follows. The samples were fractionated on an agarose gel of appropriate density (e.g., a 1.0% agarose gel was used to analyze plasmid DNA, while a 1.5% agarose gel was used to analyze RNA). The fractionated nucleic acid was visualized using a fluorescent label or by dying the gel with a DNA sensitive stain, such as ethidium bromide or silver staining. The resulting fractionated, visualized nucleic acid was either photographed or visualized using a fluorimager and the resulting image printed out using a laser printer.

In some cases, size standards were fractionated on the same gel as the target nucleic acid, and used to determine the approximate size of the target nucleic acid. In every case where a gel assay was done, the photograph or fluorimage of the fractionated nucleic acid was inspected for contamination by non-target nucleic acids. For example, images of fractionated samples of plasmid DNA were inspected for RNA, which runs considerably faster than DNA on the same gel, and for chromosomal DNA, which runs considerably slower than plasmid DNA on the same gel. Images of isolated plasmid DNA were also inspected to determine whether most of the plasmid DNA shown in the image is intact, supercoiled plasmid DNA.

Example 2

Absorption Spectrophotometry

Samples of target nucleic acids isolated from various media, as described below, were also analyzed using absorption spectrophotometry. Absorption measurements were taken at wavelengths of 260, 280, and 230 nanometers (nm). $A_{260}/A_{280}$ absorption ratios were computed from the measurements. An $A_{260}/A_{280}$ of greater than or equal to 1.80 was interpreted to indicate the sample analyzed therein was relatively free of protein contamination. The concentration of nucleic acid in each sample was determined from the absorption reading at 260 nm ($A_{260}$).

Example 3

Synthesis Of Porous Silica Magnetic pH Dependent Ion Exchange Particles

Various pH dependent ion exchange ligands were attached to porous silica magnetic particles, according to the following procedures. The silica magnetic pH dependent ion exchange particles synthesized as described herein were used to isolate target nucleic acids, as described in subsequent Examples, below.

A. Preparation of Glycidyl Modified Silica Magnetic Particles

1. Silica magnetic particles were activated by heating under vacuum at 110° C. overnight.
2. 10 g of the activated particles were suspended in 100 ml of toluene in a flask, and 3.2 ml of 3-glycidylpropyltrimethoxysilanewas added thereto.
3. The flask containing the mixture was fitted with a condenser and the reaction was refluxed for 5 hr. After cooling to room temperature, the reaction mixture sat for 48 hr at room temperature.
4. The reaction mixture was then filtered and the retentate, including glycidyl-modified silica magnetic particles produced in the reflux reaction, were washed with toluene (2×100 ml), hexanes (2×100 ml) and ethyl ether (1×150 ml). The washed product was then left to dry in the air.
5. A small portion of the product was further dried in a 110° C. oven and submitted for elemental analysis. The results (% C 0.75; % H 0.58) are consistent with glycidyl modification of silica gel particles, as illustrated in Formula (III), below. The wavy line in this and other formulae depicted herein and in the remaining Examples below represents the surface of a solid phase, a porous silica magnetic particle in this particular Example.

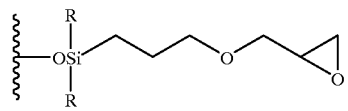

(XVI)

wherein, R is —OH, OCH₃, or —OCH₂CH₃.

6. The glycidyl-modified silica magnetic particles produced as described above were then further modified by the linkage of an amino acid, such as histidine, alanine, or cysteine to the particles, by reaction with the terminal ring of the glycidyl moiety, as described below.

B. Synthesis of Glycidyl-Histidine Modified Silica Magnetic Particles 1. 2.0 g. of D,L-histidine was dissolved in a mixture of 20 ml of tetrahydrofuran and 20 ml of water by heating the solution to reflux.
2. To this solution, 2 g of glycidyl-modified silica magnetic particles was added and the resulting suspension was refluxed overnight (18 hr).
3. After cooling to room temperature the reaction mixture was filtered, and the retentate, which included glycidyl-histidine modified silica magnetic particles, was washed once with 100 ml of acetone, three times with 150 ml of water, and once with 150 ml of ether. The solid was air dried.
4. A small portion of the dried solid from step 3 was further dried at 110° C. and submitted for elemental analysis. Results: % C 1.35; % H 0.68; % N 0.50. This results are consistent with glycidyl-histidine linkage, such as is as shown in Figure (XVII), below:

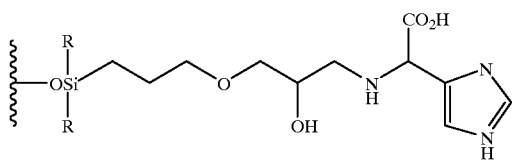

(XVII)

wherein, R is —OH, OCH$_3$, or —OCH$_2$CH$_3$.

C. Synthesis of Glycidyl -Alanine Modified Silica Magnetic Particles
1. 3-(3-pyridyl)-D-alanine (1 g) was dissolved in 20 ml of water.
2. To this solution 2 g. of glycidyl-modified silica magnetic particles were added, and the resulting mixture was refluxed overnight.
3. After cooling, the reaction mixture was filtered and washed twice with water, and once with ethyl ether.
4. Elemental analysis of a sample of the product from step 3 showed: % C 0.98; % H 0.56; % N 0.20. This result is consistent with glycidyl-alanine modification, as illustrated in formula (XVIII), below:

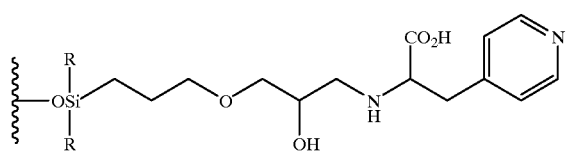

(XVIII)

wherein, R is —OH, OCH$_3$, or —OCH$_2$CH$_3$.

D. Synthesis of Glycidyl -Cysteine Modified Silica Magnetic Particles
1. 1 g of S-[2-(4-Pyridyl)ethyl]-L-cysteine was suspended in 20 ml of water, and heated to dissolve the material.
2. To this solution 2.5 g of glycidyl-modified silica magnetic particles were added, and the resulting mixture was refluxed overnight.
3. After cooling the reaction mixture was filtered and washed three times with water and ethyl ether. The material was air dried.
4. Elemental analysis of the material from step 3 showed: % C 1.08; % H 0.42; % N 0.16. This results are consistent with glycidyl-cysteine modification of silica magnetic particles, as according to formula (XIX), below:

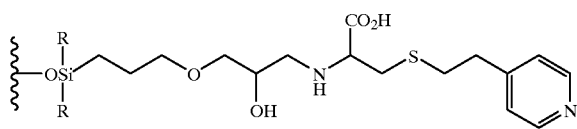

(XIX)

wherein, R is —OH, —OCH$_3$, or —OCH$_2$CH$_3$.

Example 4

Synthesis of Non-Porous Magnesil, Glass Fiber, and Silica Gel Glycidyl-Linked pH Dependent Ion Exchange Solid Phases A. Synthesis of Glycidyl-Histidine Modified Non-Porous Silica Magnetic
1. Glycidyl Modification: 6 ml of non-porous silica magnetic particles (Part No. SMR22-552, provided by W. R. Grace) were suspended in 6 ml of toluene, and 0.7 ml of 3-Glycidylpropyltrimethoxysilane was added to the suspension. The resulting mixture was placed on a roto-evaporator and allowed to react overnight. The reaction mixture was filtered and the retentate, including the modified silica magnetic particle product, was washed once with 20 ml of methylene chloride and once with 20 ml of ethyl ether. The product was dried under vacuum in a desiccator over phosphorous pentoxide. Elemental analysis showed: % C 0.3; % H 0.63. This result is consistent with glycidyl modification, as shown in formula (XVI), above.
2. Histidine Linkage: 0.5 g of D,L-histidine was dissolved in a mixture of 4 ml of tetrahydrofuran and 6 ml of water. 1.2 g of glycidyl-modified silica magnetic particles was added to the mixture; and the resulting suspension was refluxed for 5 hr. After cooling to room temperature the reaction mixture was filtered, the solid washed once with 50 ml of methanol and 50 ml. of ethyl ether. The product was dried under vacuum in a desiccator over phosphorous pentoxide. Elemental analysis revealed: % C 0.44; % H 0.64; % N 0.0. This result is consistent with glycidyl linkage of histidine to the non-porous silica magnetic particles, according to formula (XVII), above.

B. Synthesis of Glycidyl-Histidine Modified Glass-Fibers
1. Glycidine Modification: 0.7 g of glass fiber filters (Ahlstrom-122; Ahlstrom Filtration, Inc., Helsinki, Finland.) were suspended in 15 ml of toluene, and 1.0 ml of 3-glycidylpropyltrimethoxysilane was added to the suspension. The resulting mixture was incubated at room temperature for 48 hr. The solution was removed from the resulting modified glass fiber filter products by pipetting. The filter products were washed twice with 30 ml of methylene chloride, then soaked in methylene chloride for 30 min, and washed two more times with 30 ml. each of methylene chloride. This process of soaking and washing was repeated. The filters were dried under vacuum on a roto-evaporator.
2. Histidine Linkage: 0.6 g of D,L-histidine was dissolved in a mixture of 10 ml of tetrahydrofuran and 15 ml of water. This solution was added to the filters and the resulting suspension was refluxed for 20 hr. After cooling to room temperature the liquids were removed from the reaction by pipetting and the filters were washed extensively with water and with methanol. The washed filters were air dried overnight. Elemental analysis of the end product showed: % C 0.55; % H 0.16; % N 0.0. These results are consistent with glycidyl-histidine linkage, according to formula (IV), above.

C. Synthesis of Glycidyl-Histidine Modified Silica Gel

1. Glycidine Modification: 10.0 g of Silica Gel 110HP [Chromatographic Silica Grade 110HP from W. R. Grace (Baltimore, Md.)] was suspended in 45 ml of toluene, and 5.0 ml of 3-glycidylpropyl-trimethoxysilane was added to the suspension. The resulting mixture was placed on a roto-evaporator overnight. The reaction mixture was filtered and the solid product was washed once with 20 ml of methylene chloride and once with 20 ml of ethyl ether. The product was dried under vacuum in a desiccator over phosphorous pentoxide. Elemental analysis: % C 7.75; % H 1.67. These results are consistent with glycidine modification.

2. Histidine Linkage: 10 g of all of the above modified silica was suspended in 30 ml of tetrahydrofuran and 50 ml of water. To this solution 3.8 g of D,L Histidine was added and the resulting suspension was refluxed overnight (about 18 hr). After cooling to room temperature the reaction mixture was filtered, washed once with 200 ml of methanol and once with 50 ml of ethyl ether. The resulting product was dried under vacuum in a desiccator over phosphorous pentoxide. Elemental analysis revealed: % C 9.88; % H 1.92; % N 1.68. These results are consistent with glycidyl-histidine modification, according to formula (IV), above.

Example 5

Preparation of Porous Silica Magnetic Urea-Linked pH Dependent Ion Exchange Particles A. Silica Magnetic Particles Linked to Histidine Through Urea 1. Modification with Urea: 5 g of histidine ethyl ester dihydrochloride was suspended in 50 ml of chloroform and 4.0 ml of triethylamine. 4.8 g of 3-isocyanatopropyl-trimethoxysilane was added to this solution drop-wise, via an addition funnel, and the resulting silane/chloroform solution was stirred overnight. 2.0 g of porous silica magnetic particles were suspended in 25.0 ml of the silane/chloroform solution, and this mixture was placed on a roto-evaporator for 20 hr. The resulting reaction mixture was filtered, and the retentate, which included silica magnetic particles modified in the reaction, was washed once with 50 ml of chloroform and once with 50 ml of ethyl ether. The washed product was dried in a desiccator under vacuum over phosphorous pentoxide. Elemental analysis revealed: % C 2.38; % H 0.96; % N 0.81. These results are consistent with results one would expect from a silica magnetic particles modified with urea.

2. 1.0 g of the modified particles was suspended in 5% HCl and stirred for 4 hr. The particles were separated from the HCl solution, washed with water, resuspended in 25 ml of water, and filtered. The retentate, which included the modified silica magnetic particles, was washed once with 50 ml of water, once with 50 ml of methanol, and once with 50 ml of ethyl ether. The washed solid was dried under vacuum in a desiccator over phosphorous pentoxide. Elemental analysis showed: % C 1.59; % H 0.84; % N 0.55. These results are consistent with what one would expect from a silica magnetic particle linked to histidine via urea, as illustrated in formula (XX), below:

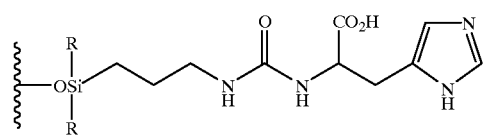

(XX)

wherein, R is —OH, —OCH$_3$, or —OCH$_2$CH$_3$.

B. Synthesis of Silica Magnetic Particles Linked to Histamine and Propionate

1. Synthesis of N-2-(4-Imidazole)-ethyl-N'-3-propyltriethoxysilylurea: 4.5 g of histamine was suspended in 50 ml of Chloroform. 9.8 g. of 3-Isocyanatopropyltrimethoxysilane was added drop-wise to the suspension, via an addition funnel, and the resulting reaction stirred overnight. After this period the reaction was evaporated to dryness. The product was not further purified. Results of analysis of this intermediate product using nuclear magnetic resonance spectroscopy (NMR) were consistent with what one would expect from N-2-(4-Imidazole)-ethyl-N'-3-propyltriethoxysilylurea. Specifically, NMR (CD3OD) results found were: 7.6 ppm (s, 1H); 6.8 (s, 1H); 4.7 (broad s, 4H); 3.8 (q, 4H); 3.6 (q, 1H) 3.36 (t, 2H); 3.30 (m, 1H); 3.07 (t, 2H); 2.72 (t, 2H); 1,55 (m, 2H); 1.2 (m, 6H).

2. Linkage of Histamine via Urea: 1.0 g of silica magnetic particles was suspended in ml of chloroform, and 1.2 g of the N-2-(4-Imidazole)-ethyl-N'-3-propyltriethoxysilylurea produced in step 1, above, was added to the suspension. The resulting mixture was placed on a roto-evaporator for 48 hr. The reaction was filtered and resuspended in 40 ml of Chloroform. The solid was filtered and washed with chloroform and ethanol. The solid was dried in a desiccator under vacuum over phosphorous pentoxide for 2 hr. Elemental analysis results (% C 5.46; % H 1.16; % N 2.35) were consistent the results one would expect to obtain from silica magnetic particles modified with histamine.

3. Methyl Propionate Modification: 1 g of the entire amount of histamine modified silica magnetic particles from step 2, above, was suspended in 10 ml of toluene and 1.0 ml of 2-(carbomethoxy)ethyltrichlorosilane was added drop-wise with stirring. The resulting reaction mixture stirred for 2 hr. After this time the solid was filtered and washed with chloroform and ethanol. The product was dried under vacuum for 1 hr in a desiccator over phosphorous pentoxide. Elemental analysis results (% C 7.24; % H 1.52; % N 2.07) were consistent with methyl propionate modification of histamine modified particles.

4. Removal of Methyl Group from the Propionate Residues: 1 g of silica magnetic particles modified in Step 3 was suspended in 5% HCl and stirred for 4 hrs. The reaction products were separated from the solution by filtration. The retentate of reaction product, which included the modified particles, was washed with water and methanol. The washed product was dried under vacuum in a desiccator over phosphorous pentoxide. Elemental analysis results (% C 6.14; % H 1.37; % N 1.47) were consistent with silica magnetic particles linked to histamine through urea and also modified by propionate, according the formula (XXI), below:

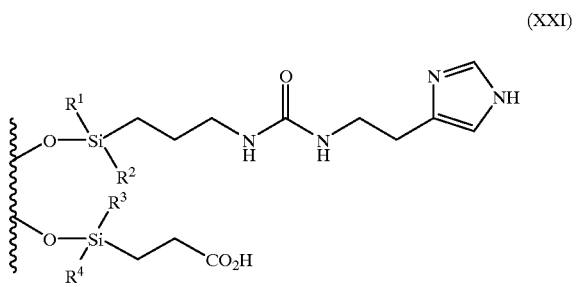

(XXI)

wherein, $R^1$ and $R^3$ are, independently, —OH, —OCH$_3$, or —OCH$_2$CH$_3$; $R^2$ is —(OSiR$^2{}_2$)$_y$—R$^2$, wherein y is at least 0; and $R^4$ is —OsiR$^3{}_2$)$_z$—R$^3$, wherein z is at least 0.

C. Synthesis of Silica Magnetic Particles Linked to Histidine and Propionate

1. Histidine was covalently attached to silica magnetic particles via a urea linkage, using a procedure similar to that used to attach histamine in part A of this Example, above.
2. The same final two steps used to covalently attach propionate to the urea-linked histamine particles in part B of the Example, above were used to covalently attach propionate to the silica magnetic particles linked to histidine via propionate.

Example 6

Preparation of Cleared Lysate of Plasmid DNA

E. coli bacteria cells, DHα strain, were transformed with pGL3-Control Vector (Promega) plasmid DNA, and grown in an overnight culture of Luria Broth ("LB") medium at 37° C., then harvested by centrifugation.

The following solutions were used to prepare a lysate of the harvested cells, as described below:
Cell Resuspension Solution:
  50 mM Tris-HCl, pH 7.5
  10 mM EDTA
  100 μg/ml DNase-free ribonuclease A (RNase A)
Wizard® Neutralization Buffer (Promega Corp.):
  1.32 M KOAc (potassium acetate), pH 4.8
Cell Lysis Solution:
  0.2 M NaOH
  1% SDS (sodium dodecyl sulfate)
A cleared lysate of the transformed cells was produced as follows:
1. The cells from 1 to 10ml of bacteria culture were harvested by centrifuging the culture for 1–2 minutes at top speed in a microcentrifuge. The harvested cells were resuspended in 250 μl of Cell Resuspension Solution, and transferred to a microcentrifuge tube. The resulting solution of resuspended cells was cloudy.
2. 250 μl of Cell Lysis Solution was then added to the solution of resuspended cells and mixed by inversion until the solution became relatively clear, indicating the resuspended cells had lysed.
3. 350 μl of Wizard® Neutralization Buffer was added to the lysate solution, and mixed by inversion. The lysate became cloudy after the Neutralization Solution was added.
4. The solution was then spun in a microcentrifuge at top speed (about 12,000 G) for 10 minutes to clear the lysate.

Example 7

Isolation of Plasmid DNA Using Porous Silica Magnetic Glycidyl-HistidinepH Dependent Ion Exchange Particles All preps were processed in 1.5 ml tubes, and all steps were performed at room temperature:

1. The cleared lysate from step 5 of Example 6 was transferred to a clean 1.5 ml tube containing 150 μl of an pH dependent porous silica magnetic ion exchange particles (15 mg of particles) linked to histidine through a glycidyl moiety, wherein the particles prepared as described in Example 3B. The resulting mixture of particles and solution was vortexed, and incubated at room temperature for 5 minutes.
2. The silica magnetic ion exchange particles contained in the tube were held against the inner side-wall of the tube by magnetic force, while the tube cap and side-wall were washed with the lysate solution four times by inversion, and allowed to sit for 1 minute at room temperature. The solution was removed and discarded.
3. The particles tube and cap were washed with 1.0 ml nanopure water.
4. Magnetic force was used to hold the silica magnetic particles in the tube while liquid in the tube was removed therefrom and from the tube cap. The liquid was discarded.
5. The particles were resuspended by vortexing in 300 μl of 66 mM potassium acetate and 800 mM NaCl (pH 4.8). Step 3 was repeated.
6. Step 5 was repeated three times, for a total of four salt washes.
7. The silica magnetic particles remaining in the tube were resuspended in 1.0 ml of nanopure water.
8. The silica magnetic ion exchange particles were separated from the water by magnetic force. The tube cap and side-wall was washed with water by tube inversion (4×), and allowed to sit 1 minute.
9. Liquid was removed from the tube and cap.
10. Steps 7–9 were repeated for a total of 2 washes, with water.
11. 100 ul of 10 mM Tris pH 8.0 was added to the tube to elute the DNA, and the tube was vortexed thoroughly.
12. The silica magnetic ion exchange particles were separated from the eluent by magnetic force, and the eluent removed to a clean tube.

Analytical analysis of the eluent from step 12 showed that plasmid DNA was obtained which was relatively free of contaminating proteins or other nucleic acids. Specifically, analysis of the eluent using gel electrophoresis according to the procedure set forth in Example 1, above, showed no RNA or chromosomal RNA contamination. Analysis of the eluent using absorption spectroscopy as described in Example 2, showed the yield of pGL-3 plasmid DNA to be 30 μg. Absorbance ratio results ($A_{260}/A_{280}$ ratio of 1.84) indicated the plasmid DNA isolated according to the procedure described above was free of protein contamination.

Example 8

Isolation of Plasmid DNA from a Cleared Lysate Using Glycidyl-Histidineglass Fibers A cleared lysate from 5 ml of an overnight culture of DH5α cells transformed with pGL3 Control Vector plasmid DNA was prepared as described in Example 3. The cleared lysate was added to a column containing 42 mg of Ahlstrom 121 glass fiber modified by glycidyl-histidine, as described in Example 4B, above. After 10 minutes of binding time, the column was centrifuged to remove the alkaline lysate solution. The column was then washed using 700 μl of nanopure water, which was removed by column centrifugation. This water wash was repeated twice (for a total of three washes). The DNA was eluted with 100 μl of 10 mM Tris pH 8.0, and the solution collected into a 1.5 ml tube by column centrifugation. The eluted DNA was examined by gel electrophoresis according to the procedure set forth in Example 1, and no RNA or chromosomal DNA contamination was detected. Analysis by atomic absorbsion spectroscopy showed a DNA yield of 36 µg, and an $A_{260}/A_{280}$ ratio of 1.86.

The column was washed with 400 µl of 10 mM Tris pH 8.0 (which was removed by column centrifugation), and washed again with 2×700 µl of 100 mM Tris, 2.0 M NaCl (also removed by column centrifugation). The column was then washed with 700 µl of nanopure water, (removed by column centrifugation), and air dried for 12 hours at room temperature.

The column was reused, following the same procedure as outlined above. The resulting DNA again showed no visible RNA by gel electrophoresis, and a DNA yield of 30 ug and an $A_{260}/A_{280}$ ratio of 1.84.

Example 9

Isolation of Plasmid DNA from a Cleared Lysate Using Non-Porous Glycidyl-Histidine Ion Exchange Particles Functionalized with Glycidyl Histidine A cleared lysate of DH5α cells transformed with pGL3 Control Vector plasmid DNA was prepared as described in Example 6, except 500 ul of Wizard® Neutralization Buffer was added to the lysed cells in step 3, rather than 350 ul. Plasmid DNA was isolated from the cleared lysate using non-porous glycidyl-histidine silica particles prepared as described in Example 4A, as follows:

The cleared lysate was combined with 15 mg of the glycidyl-histidine non-porous silica particles in a 3 ml syringe barrel, and allowed to sit at room temperature for 1 hour.

The lysate was then pushed through the syringe barrel, by positive pressure. Two 1.0 ml washes with nanopure water were performed, using positive pressure to remove the liquid. Then 100 ul of 10 mM Tris, pH 8.0 was used to elute the DNA. The eluted DNA was removed by positive pressure into a clean 1.5 ml tube.

Analysis by gel electrophoresis, according to the procedure of Example 1, showed the eluent to contain supercoiled plasmid DNA, with no evidence of contamination with chromosomal DNA or RNA. Absorption analysis of the eluent, according to the procedure of Example 2, showed a yield of 10 mg of DNA, and an absorbance ratio of $A_{260}/A_{280}$ of 1.61.

Example 10

Isolation of Plasmid DNA from a Cleared Lysate Using Porous Silica Magnetic Gylcidyl-Alanine Plasmid DNA was isolated from DH5α E. coli bacteria cells transformed with pGEM-3Zf+ DNA, as follows. Preps were processed in 1.5 ml tubes. All steps were performed at room temperature, except where indicated otherwise below.
1. 2.5 ml of Wizard® Resuspension Solution was added to a 50 ml pellet of transformants, and vortexed vigorously to resuspend cells.
2. 265 µl of resuspended cells were added to two tubes.
3. 250 µl of Wizard® Lysis Buffer was added per tube, and gently mixed to avoid sheering genomic DNA.
4. 350 µl of Wizard® Neutralization Solution was added per tube, and mixed gently.
5. The tubes were centrifuged at 14 k rpm for 10 minutes.
6. The cleared solution was removed and placed in a clean 1.5 ml tube containing 150 ul of 100 mg/ml (15 mg) silica magnetic glycidyl-alanine particles prepared as described in Example 3C, above. The resulting mixture was vortexed, and incubated 5 minutes.
7. The particles were separated from the mixture, using a magnetic separator. The tube caps were washed by tube inversion (4×), and incubated 1 minute.
8. Liquid was removed from tubes, including caps.
9. Tubes were washed with 1.0 ml of nanopure water.
10. Steps 7 and 8 were repeated.
11. Steps 9 and 10 were repeated twice, for a total of 3 washes.
12. An elution buffer of 100 µl of 20 mM Tris-HCl, pH 9.5, was added to each tube. The particles and buffer were mixed well to allow plasmid DNA which had adsorbed to the particles to elute therefrom.
13. The particles were separated from the resulting eluent by magnetic force. The eluent solution in each tube was transferred to a clean tube.

Duplicate isolations conducted according to the procedure described above yielded 21.7 µg (A260/280 of 1.86) and 16.1 µg (A260/280 of 1.89) of plasmid DNA. No RNA was visible by analysis using gel electrophoresis.

Example 11

Comparison of Counterion Conditions Required to Elute Plasmid DNA From Silica Magnetic Urea-Linked Histamine, and Silica Magnetic Urea-Linked Histamine and Propionate Bimodal ion Exchange Particles at Various pH's The minimum amount of sodium chloride and a buffer required to elute plasmid DNA from each of two different types of silica magnetic pH dependent ion exchange particles was assayed at each of several different pH's, according to the following procedure. One of the two types of particles used in this assay was silica magnetic particles linked to histidine through a urea residue (referred to in the present Example as "urea-histidine IE particles"), prepared as described in Example 5A, above. The other type of particle used in this Example was silica magnetic particles linked directly to propionate and linked to histamine through a urea residue (hereinafter, "bimodal-histamine -propionate IE particles") prepared as described in Example 5B, above. Elemental analysis of the bimodal-histamine -propionate IE particles showed 260 µmoles of histamine and 900 µmoles of propionate.

Cleared lysates were prepared from the DH5α strain of E. coli bacteria cells transformed with pGL3-Control Vector (Promega), as described in Example 6, above, modified as follows. Cells from 50 ml of an overnight culture of the transformants were harvested by centrifugation, and resuspended in 2.5 ml of Wizard® Resuspension Solution. The cells were lysed by adding 2.5 ml of Wizard® Lysis Solution to the resuspended cells. 3.5 ml of Wizard® Neutralization Solution was added to the resulting lysate. The lysate was cleared by centrifugation, and the supernatant transferred to a sterile 50 ml tube.

The urea-histidine IE particles and bimodal-histamine-propionate IE particles were tested and compared to one another for their capacity to bind to and release plasmid DNA from the cleared lysate prepared as described immediately above. The elution solution used to isolate plasmid DNA with each of the two types of particles varied, with a pH ranging between pH 4.2 and 9.5:
1. 700 µl of the cleared lysate was added to each 1.5 ml microfuge tube in each of four sets of two samples for each of the two types of particles tested. Each 1.5 ml microfuge tube contained 150 μl of either of the two types of particles (15 mg). Each tube was capped and mixed by inversion. The resulting suspension was incubated at room temperature for 5 minutes.

2. The particles and solution were separated by magnetic force, and the solution removed from each tube. 1.0 ml of nanopure water was added to each tube, used to wash the particles, separated from the particles by magnetic force, and removed from the tube. For all the sets of samples except those to be eluted at a pH of below pH 5 (e.g. samples to be eluted at 4.2 or 4.8), the water wash was repeated.

3. The particles were resuspended in 300 μl of the putative elution solution. The particles were magnetically separated, and the solution carefully removed to a clean 1.5 ml tube. The salt concentration of the elution solution has modified, by addition of either water or 5 M NaCl, to a final concentration of 1 M NaCl. The DNA (if present) was concentrated by precipitation with 1.0 ml of −20° C. ethanol. The DNA was pelleted by centrifugation in a microfuge at 12,000×g for 10 minutes. The pellets were dried to remove ethanol, and resuspended in 100 μl of 10 mM Tris HCl pH 9.5.

4. The particles remaining from step 3 were washed once with 1.0 ml nanopure water, and then treated as the particles at the beginning of step 3. In this way, a variety of elution solutions were tested, in a stepwise fashion, using the same DNA bound particles.

5. For elution conditions above pH 8.0, 100 μl of 10 mM Tris HCl was used in the case of the bifunctional IE particles. Similar testing of the urea-histamine IE particles showed no DNA elution at 10 mM Tris HCl, even at pH 9.5. The eluted DNA was examined by gel electrophoresis to determine the minimum counterion concentration need for DNA elution. Once the approximate concentration was determined, the procedure was repeated to confirm the concentration of potassium acetate and NaCl at pH 4.8, and the concentration of Tris HCl and NaCl at pH 7.3, and pHs above 7.3.

Elution conditions used on each set of samples prepared as described above are shown in Table 1, below:

TABLE 1

| pH | Urea-Histidine IE Particles | Bifunctional IE Particles |
|---|---|---|
| 4.2 | 33 mM KOAc/2.15M NaCl | |
| 4.8 | | 33 mM KOAc/1.7M NaCl |
| 7.3 | 100 mM Tris HCl/600 mM NaCl | 100 mM Tris/300 mM NaCl |
| 8.0 | 100 mM Tris/300 mM NaCl | 100 mM Tris/no NaCl |
| 8.7 | | 100 ul of 10 mM Tris HCl |
| 9.5 | 100 ul of 50 mM Tris HCl | |

The results above demonstrate that the addition of propionate groups to urea-histidine IE particles reduces the amount of counterion concentration required to elute DNA from such particles.

Example 12

Isolation of PCR Amplified DNA from Unincorporated Nucleotides and Primers, Using Non-Porous Silica Magnetic Glycidyl-Histidine pH Dependent Ion Exchange Particles. Similar Purification of PCR Amplified DNA Using Porous Silica Magnetic Glycidyl Cysteine pH Dependent Ion Exchange Particles The human APC (Adenomatous Polypoptosis Coli) gene was amplified in a PCR amplification reaction, wherein human genomic template DNA was added to a reaction mix containing:

40 ul 10× AmpliTaq® PCR buffer (no Mg++) [Perkin Elmer];

40 ul 25 mM $MgCl_2$;

13 ul 10 mM dNTP mix;

13 ul APC primers (50 pmoles/μl), with nucleotide sequences: 5'GGA TCC TAA TAC GAC TCA CTA TAG GAA CAG ACC ACC ATG CAA ATC CTA AGA GAG AAC AAC TGT C3' [SEQ ID NO: 1], and 5'CAC AAT AAG TCT GTA TTG TTT CTT 3' [SEQ ID NO: 2];

6.4 ul AmpliTaq® [Perkin Elmer]; and 273.6 ul of nanopure water [total=392 μl].

The amplification reaction was run for 35 cycles on a Perkin Elmer 4800 thermocycler.

A 1.8 kb DNA product was the result of the amplification.

The resulting PCR amplified gene was isolated from other components in the reaction mix, above according to the following isolation procedure:

1. 20 μl of the PCR reaction mix was added to 200 μl of 66 mM KOAc+900 mM NaCl, pH 4.8, and mixed. Then, 20 μl (2 mg) of non-porous glycidyl-histidine silica magnetic particles was added.

2. After mixing, the solution was incubated for 5 minutes at room temperature. The particles were separated by use of a magnetic separator, and the solution was removed to a clean 1.5 ml tube.

3. The particles were resuspended by vortexing in 200 μl of nanopure water, and separated from the resulting solution. The particles were separated using a magnetic separator, the cap and side-wall of the tube were washed by inverting the tube, and the solution was removed from the cap and tube, and placed in a clean 1.5 ml tube.

4. The PCR amplified DNA was eluted in 20 μl of 10 mM Tris HCl pH 8.0. The particles were separated by magnetic force and the eluted DNA was removed to a clean 1.5 ml tube.

5. Using gel electrophoresis (see Example 1), the solutions obtained from steps 2, 3, and 4 were compared with a sample of the original PCR reaction. The solution from steps 2 showed no visible PCR amplified DNA. The solution from step 2 showed a small amount (about 10% of the initial amount) of the PCR DNA. The solution from step 4 showed an amount of PCR DNA >80% of the initial amount in the reaction mix, and no visible unincorporated primers and nucleotides, as seen in the initial PCR reaction solution.

The same procedure was followed using MagneSil™ (no histidine ligand) porous particles, and resulted in no visible DNA at the end of step 4.

The same amplification mixture was purified using porous silica magnetic glycidyl-cysteine pH dependent ion exchange particles and using silica magnetic particles (as a control), according to the following procedure:

1. Three 1.5 ml tubes were set up with 20 ul of amplification mixture mixed with 200 ul of 33 mM KOAc/400 mM NaCl, pH 4.8. To tubes 1 and 2, 20 μl (2 mg) of Mag-IE-glycidyl-cysteine was added and mixed. To tube 3, 20 μl of Magnesil™ particles was added and mixed.

2. Each tube was incubated 10 minutes at 20° C., and the particles in each tube separated from the solution in each tube by magnetic force, for 2 minutes.

3. The solution from each tube was removed. The solutions from tubes 1 and 2 were processed according to steps 4–5, below. The particles in tube 3 were resuspended in 33 mM KOAc/ 400 mM NaCl, pH 4.8, magnetically separated for 2 minutes, and the solution removed and processed according to steps 4–5, below.

4. The particles were resuspended in 200 ul of nanopure water, magnetically separated, and the solution removed from the tube.
5. DNA was eluted in 20 ul of 50 mM Tris HCl pH 9.5

Figure 4:
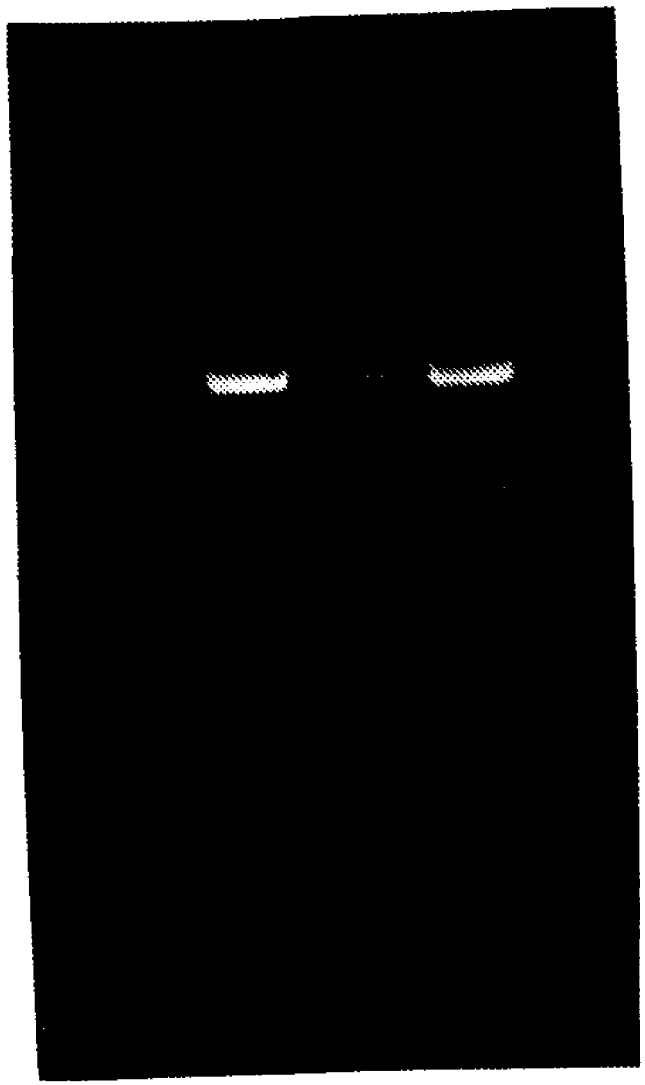
FIG. 4 is a reproduction of a photograph of amplified DNA isolated with Magnasil™ and with pH dependent silica magnetic particles, as described in Example 12, then fractionated by gel electrophoresis, and stained with ethidium bromide.

Aliquots of the original amplification reaction products and of the eluents from Magnesil™ (tube 1, above) and from Mag-IE-glycidyl-histidine (tubes 2–3 above) were analyzed by gel electrophoresis, as described in Example 1, above. The resulting gel was stained with ethidum bromide, and a photograph thereof taken under UV light. FIG. 4 shows the gel, with:, Lane 1: Eluent from the Magnesil™ particles (tube 1, above).

Lane 2: Eluent from the Mag-IE-glycidyl-histidine particles (tube 2, above), with no wash step prior to transfer of the particles from the amplification reaction solution to nanopure water in step 4, above.

Lane 3: Eluent from the Mag-IE-glycidyl-histidine particles (tube 3, above), after washing the particles in 33 mM KOAc/400 mM NaCl, pH 4.8 prior to transfer to nanopure water in step 4, above.

Lane 4: Aliquot of the amplified DNA reaction mixture.

Note that the amplified DNA reaction mixture includes bands other than the desired amplification product. The Magnesil™ particles appear to have failed to isolate any detectable quantity of the amplified DNA fragments, as no bands are visible in lane 1 of FIG. 4. Both isolation procedures with Mag-IE-glycidyl-histidine produced amplified DNA isolated from low molecular weight species (the band below the primary band in lane 4). However, considerably more amplified DNA was produced from tube 2, without the additional wash step, than was isolated from tube 3 with the additional wash step.

Example 13

Isolation of Human Genomic DNA from Buccal Swabs, Using Non-Porous Silica Magnetic Glycidyl-Histidine particles Genomic DNA was isolated from buccal swabs using non-porous silica magnetic glycidyl-histidine ion exchange particles, synthesized as described in Example 3B, above, as follows:

Tissue samples were obtained from two inner cheek areas of human subjects, using cotton swabs (buccal collection), and the swabs were allowed to sit at room temperature for 10 minutes, with occasional swirling, in 700 µl of a cell lysis buffer (75 mM Na Citrate pH 5.0/1.5% Tween) in a 1.5 ml microfuge tube. The swabs were removed and the liquid in the swabs was pressed out by running it over the opening of the tube, pressing the swab into the interior side of the tube.

30 µl of proteinase K (18 mg/ml) was added to each tube, and 50 µl (5 mg) of non-porous silica magnetic glycidyl-histidine particles was added per tube, and mixed well. Samples were incubated at room temperature for 5 minutes, with occasional mixing by tube inversion.

The tubes were placed on a magnetic rack to allow separation of the solution and particles, and the solution was removed from the tube.

The particles were washed twice with 1.0 ml of nanopure water. After removal of the second 1 ml of water, the DNA was eluted in 40 µl of 20 mM Tris HCl pH 9.5, at 65 °C. for 5 minutes.

Magnetic force was used to separate the particles from the eluted DNA.

The eluted DNA was examined by gel electrophoresis, as described in Example 1, above, and compared to a control sample of a known amount of genomic DNA to estimate the quantity of DNA eluted. Each 40 µl sample of eluted DNA was found to contain greater than 100 ng of genomic DNA.

Example 14

Comparison of Counterion Conditions Required to Elute Plasmid DNA from Silica Magnetic Urea-Histidine pH Dependent Ion Exchange Particles and Silica Magnetic Urea-Histidine Propionate Bimodal pH Dependent Ion Exchange Particles The minimum amount of sodium chloride and a buffer required to elute plasmid DNA from each of two different types of silica magnetic pH dependent ion exchange particles was determined at each of several pH's, according to the following procedure. Silica magnetic urea-histidine IE particles prepared as described in Example 5A, and silica magnetic bimodal urea-histidine -propionate IE particles prepared as described in Example 5C were used to isolate plasmid DNA from a cleared lysate, as follows.

Cleared lysates were prepared as described in example 11. The procedure for comparing the elution profiles of the two particles was as described in example 11. The pHs tested were 4.8, 7.3, and 9.5. The results obtained are shown in Table 3, below:

TABLE 3

| MAGNETIC PARTICLE AND pH CONDITIONS | ELUTION/NON-ELUTION CONDITIONS |
|---|---|
| Urea-histidine IE particles, pH 4.8 | DNA eluted in 33 mM KOAc/1.45M NaCl, did not elute in 33 mM KOAc/1.40M NaCl |
| Bimodal urea-histidine-propionate IE particles, pH 4.8 | DNA eluted in 33 mM KOAc/0.80M NaCl, did not elute in 33 mM KOAc/0.70M NaCl |
| Urea-histidine IE particles, pH 7.3 | DNA eluted in 100 mM Tris HCl, did not elute in 80 mM Tris HCl |
| Bimodal Urea-histidine-propionate IE particles, pH 7.3 | DNA eluted in 60 mM Tris HCl, did not elute in 50 mM Tris HCl |
| Urea-histidine IE particles, pH 9.5 | Did not elute in 100 ul of 10 mM Tris HCl, but eluted in 100 ul of 100 mM Tris HCl |
| Bimodal Urea-histidine-propionate IE particles, pH 9.5 | Eluted in 100 ul of 10 mM Tris HCl |

By spectrophotometric analysis, the elutions in 100 ul of 10 mM Tris HCl at pH 9.5 yielded 30 µg ($A_{260}/A_{280}$ of 1.78) of DNA for the bimodal urea-histidine -propionate IE particles and less than 2 µg of DNA for the urea-histidine IE particles. No DNA was detected on analysis of the eluent from the urea-histidine IE particles, by gel electrophoresis. The results above indicate that the addition of propionate to the urea-histidine particles lowered the needed concentration of counter-ion (chloride) required for elution of the DNA at pH 4.8, 7.3 and 9.5.

What is claimed is:

1. A pH dependent ion exchange matrix for isolating a target nucleic acid, comprising:
   a silica magnetic particle; and
   a plurality of first ion exchange ligands, each first ion exchange ligand comprising:
      an aromatic hydrocarbon ring, wherein at least one member of the ring is an amine with a pK of less than about 9;
      a spacer covalently attached to the aromatic hydrocarbon ring, the spacer comprising a spacer alkyl chain of with an amine terminus, and an acidic moiety covalently attached to the spacer alkyl chain; and
      a linker comprising a linker alkyl chain covalently attached to the silica magnetic particle through a silica residue at a first end of the linker alkyl chain and covalently attached to the amine terminus of the spacer at a second end of the linker alkyl chain;
   wherein the matrix has a capacity to adsorb to a target nucleic acid at a first pH, and to release the target nucleic acid at a desorption pH which is higher than the first pH.

2. The matrix of claim 1, wherein the cap further comprises an aromatic hydrocarbon ring.

3. The matrix of claim 2, wherein at least one member of the aromatic hydrocarbon ring is the amine with a pK of less than about 9.

4. The matrix of claim 3, wherein the aromatic hydrocarbon ring is selected from the group consisting of pyridine, and imidazole.

5. The matrix of claim 1, wherein the amine with a pK of less than 9 has a pK of at least about 4 and up to about 6.

6. The matrix of claim 1, wherein the acidic moiety is selected from the group consisting of hydroxyl, carboxyl, and carbonyl.

7. The matrix of claim 1, wherein the spacer alkyl chain comprises two (2) to five (5) carbon atoms.

8. The matrix of claim 1, wherein the spacer is selected from the group consisting of cysteine and alanine.

9. The matrix of claim 1, wherein the aromatic hydrocarbon covalently linked to the spacer define a basic amino acid moiety selected from the group consisting of histidine and histamine.

10. The matrix of claim 1, wherein the linker alkyl chain comprises three (3) to eight (8) carbon atoms.

11. The matrix of claim 1, wherein the linker alkyl chain includes at least one member selected from the group consisting of oxygen and amine.

12. The matrix of claim 1, wherein the linker is selected from the group consisting of:
    glycidine and urea.

13. The matrix of claim 1, wherein the matrix is an anion exchanger capable of exchanging with the target nucleic acid at the first pH, and the matrix was a net neutral or negative charge at the desorption pH is not.

14. The matrix of claim 1, wherein the matrix can be reused through at least two cycles of adherence of the target nucleic acid to the matrix at the first pH and release from the matrix at the desorption pH.

15. The matrix of claim 9, wherein the linker is urea.

16. The matrix of claim 9, wherein the matrix is an anion exchanger capable of exchanging with the target nucleic acid at the first pH, neutral at a second pH which is higher than the first pH, and a cation exchanger at a third pH which is higher than the second pH.

17. The matrix of claim 9, wherein the proportion of the plurality of first ion exchange ligands and the plurality of second ion exchange ligands covalently attached to the solid phase is designed to ensure that when the matrix comes into contact with a solution comprising a target nucleic acid at the first pH, the matrix preferentially binds to the target nucleic acid.

18. The matrix of claim 9, wherein the matrix can be reused through at least two cycles of adherence of the target nucleic acid to the matrix at the first pH and release from the matrix at the desorption pH.

19. A multimodal pH dependent ion exchange matrix, comprising:

a solid support;
a plurality of first ion exchange ligands, each first ion exchange ligand comprising:
a cap comprising an amine with a pK of less than about 9;
a spacer covalently attached to the cap, the spacer comprising a spacer alkyl chain with an amine terminus; and
a linker comprising a linker alkyl chain covalently attached to the solid support at a first end of the linker alkyl chain and covalently attached to the amine terminus of the spacer at a second end of the linker alkyl chain;
a plurality of second ion exchange ligands, each second ion exchange ligand comprising:
a second alkyl chain covalently attached to the solid support at a first end of the second alkyl chain; and
a second acidic moiety covalently attached to a second end of the second alkyl chain,
wherein the matrix has a capacity to adsorb to a target nucleic acid at a first pH, and to release the target nucleic acid at a desorption pH which is higher than the first pH.

20. The matrix of claim 19, wherein the solid support is a silica based material.

21. The matrix of claim 20, wherein the silica based material is a silica magnetic particle.

22. The matrix of claim 19, wherein the solid support is porous.

23. The matrix of claim 19, wherein the solid support is non-porous.

24. The matrix of claim 19, wherein the cap further comprises an aromatic hydrocarbon ring.

25. The matrix of claim 24, wherein at least one member of the aromatic hydrocarbon ring is the amine with a pK of less than about 9.

26. The matrix of claim 24, wherein the aromatic hydrocarbon ring is selected from the group consisting of pyridine and aniline.

27. The matrix of claim 19, wherein the second acidic moiety is a carboxylic acid residue.

28. The matrix of claim 19, wherein the spacer alkyl chain comprises two (2) to five (5) carbon atoms.

29. The matrix of claim 24, wherein the aromatic hydrocarbon covalently linked to the spacer define a basic amino acid moiety selected from the group consisting of histidine and histamine.

30. The matrix of claim 19, wherein the linker alkyl chain comprises three (3) to eight (8) carbon atoms.

31. The matrix of claim 19, wherein the linker alkyl chain includes at least one member selected from the group consisting of oxygen and amine.

32. The matrix of claim 27, wherein the second pH is at least about 4.0 and up to about pH 10.0.

33. The matrix of claim 19, wherein the spacer is urea.

34. The matrix of claim 19, wherein the matrix is an anion exchanger capable of exchanging with the target nucleic acid at the first pH, neutral at a second pH which is higher than the first pH, and a cation exchanger at a third pH which is higher than the second pH.

35. The matrix of claim 34, wherein the second pH is at least about 4.0 and up to about pH 10.0.

36. The matrix of claim 19, wherein the proportion of the plurality of first ion exchange ligands and the plurality of second ion exchange ligands covalently attached to the solid phase is designed to ensure that when the matrix comes into contact with a solution comprising a target nucleic acid at the first pH, the matrix preferentially binds to the target nucleic acid.

37. A method of isolating a target nucleic acid using a multimodal pH dependent ion exchange matrix, comprising the steps of:
(a) providing a multimodal pH dependent ion exchange matrix comprising:
a solid support;
a plurality of first ion exchange ligands, each first ion exchange ligand comprising:
a cap comprising an amine with a pK of less than 9, wherein the amine is selected from the group consisting of a primary, a secondary, and a tertiary amine;
a spacer covalently attached to the cap, the spacer comprising a spacer alkyl chain with an amine terminus; and
a linker comprising a linker alkyl chain covalently attached to the solid support at a first end of the linker alkyl chain and covalently attached to the amine terminus of the spacer at a second end of the linker alkyl chain;
a plurality of second ion exchange ligands comprising:
a second alkyl chain covalently attached to the solid support at a first end of the second alkyl chain; and
a second acidic moiety covalently attached to a second end of the second alkyl chain,
wherein the matrix has a capacity to adsorb to a target nucleic acid at a first pH, and to release the target nucleic acid at a desorption pH which is higher than the first pH,
(b) providing a mixture comprising the target nucleic acid;
(c) combining the mixture and the matrix and incubate at the first pH until the nucleic acid adsorbs to the matrix, forming a complex;
(d) separating the complex from the mixture; and
(e) combining the complex with an elution solution at the desorption pH.

38. The method of claim 37, wherein the solid phase of the matrix provided in step (a) is a silica based material.

39. The method of claim 37, wherein the silica based material is glass fiber.

40. The method of claim 38, wherein the silica based material is a silica gel particle.

41. The method of claim 38, wherein the silica based material is a silica magnetic particle.

42. The method of claim 37, wherein the cap further comprises an aromatic hydrocarbon ring.

43. The method of claim 42, wherein the amine with a pK of less than about 9 is a member of the aromatic hydrocarbon ring.

44. The method of claim 37, wherein the spacer alkyl chain of the matrix provided in step (a) comprises two (2) to five (5) carbon atoms.

45. The method of claim 37, wherein the spacer of the matrix provided in step (a) is selected from the group consisting of cysteine and alanine.

46. The method of claim 37, wherein the aromatic hydrocarbon covalently linked to the spacer of the matrix provided in step (a) define a basic amino acid moiety selected from the group consisting of histidine and histamine.

47. The method of claim 37, wherein the linker alkyl chain of the matrix provided in step (a) comprises three (3) to eight (8) carbon atoms.

48. The method of claim 37, wherein the linker alkyl chain of the matrix provided in step (a) includes at least one member selected from the group consisting of oxygen, amine, and sulphur.

49. The method of claim 37, wherein the linker of the matrix provided in step (a) is selected from the group consisting of: glycidine and urea.

50. The method of claim 37, wherein the matrix provided in step (a) further comprises a first acidic moiety covalently attached to the spacer alkyl chain of each first ion exchange ligand.

51. The matrix of claim 37, wherein at least one of the plurality of second ion exchange ligands is a propionate residue.

52. The method of claim 37, wherein the mixture comprising the target nucleic acid material is obtained by disrupting biological material containing the target nucleic acid.

53. The method of claim 37, wherein the target nucleic acid material is RNA.

54. The method of claim 37, wherein the target nucleic acid is DNA.

55. The method of claim 37, wherein the plurality of first ion exchange ligands of the matrix provided in step (a) is selected from the group consisting of:

histamine via epoxide, histidine via epoxide, histidine via uiea. histidine via sulfhydryl, pyridyl alanine, pyridyl cysteine.

56. The method of claim 54, wherein the target nucleic acid is plasmid DNA.

57. The method of claim 54, wherein the target nucleic acid is genomic DNA.

58. A method of making a pH dependent ion exchange matrix, comprising the steps of:
 (a) providing a solid phase;
 (b) providing a linker comprising an alkyl chain having a first end and a second end;
 (c) combining the silica based solid phase and the linker under conditions where a covalent bond is formed between the solid phase and the first end of the linker alkyl chain, thereby producing a linker-modified solid phase;
 (d) providing an acidic aromatic amine comprising: an aromatic hydrocarbon ring, wherein at least one member of the ring is an amine; a spacer which is covalently attached to the aromatic hydrocarbon, wherein the spacer comprises a spacer alkyl chain with an amino terminus; and an acidic substituent which is covalently attached to the spacer alkyl chain; and
 (e) combining the linker-modified solid phase with the acidic aromatic amine under conditions where a covalent bond is formed between the amino terminus of the spacer alkyl chain of the acidic aromatic amine and the second end of the linker.

59. The method of claim 58, wherein the solid phase provided in step (a) is a silica based material.

60. The method of claim 59, wherein the linker is covalently attached to the solid phase in step (c) through a silica residue, wherein the silica residue is covalently attached to a first subunit and a second subunit, wherein the first subunit is selected from the group consisting of: —OH, —OCH$_3$, —OCH$_2$CH$_3$, and the second subunit is defined by the formula —(OSiR$^1{}_2$)$_x$—R , wherein R$_1$ is the same group as the first subunit, and x is at least 0.

61. The method of claim 59, wherein the silica based material is glass fiber.

62. The method of claim 59, wherein the silica based material is a silica gel particle.

63. The method of claim 62, wherein the silica gel particle is paramagnetic.

64. The method of claim 62, wherein the silica gel particle is porous.

65. The method of claim 62, wherein the silica gel particle is non-porous.

66. The method of claim 58, wherein the spacer is selected from a group consisting of cysteine and alanine.

67. The method of claim 58, wherein the aromatic hydrocarbon ring has at least five members.

68. The method of claim 58, wherein the acidic aromatic amine is an amino acid selected from the group consisting of histamine and histidine.

69. A method of making a bimodal pH dependent ion exchange matrix, comprising the steps of:
 (a) providing a solid support;
 (b) providing a first ion exchange ligand comprising:
  a cap comprising an amine with a pK of less than about 9, wherein the amine is selected from the group consisting of a primary, a secondary, or a teritary amine;
  a spacer covalently attached to the cap, the spacer comprising a spacer alkyl chain and with an amine terminus; and
  a linker comprising a linker alkyl chain having a first end and a second end, wherein the second end is covalently attached to the amine terminus of the spacer;
 (c) combining the solid phase and the first ion exchange ligand under conditions where a covalent bond is formed between solid phase and the first end of the linker alkyl chain;
 (d) providing a second ion exchange ligand, comprising a second alkyl chain and an acidic residue covalently attached thereto, wherein the acidic residue has a protective group covalently attached thereto;
 (e) combining the solid phase with the first ion exchange ligand attached thereto with a second ligand under conditions which promote formation of a covalent bond between the protected second ion exchange ligand and the solid phase; and
 (f) deprotecting the acidic residue of the second anion exchange ligand by removing the protective group therefrom.

70. The method of claim 69, wherein the second ion exchange ligand is a propionate residue.

* * * * *